US006262338B1

(12) United States Patent
Schreier et al.

(10) Patent No.: US 6,262,338 B1
(45) Date of Patent: Jul. 17, 2001

(54) RESISTANCE GENES

(75) Inventors: Peter Schreier, Köln; Thomas Herget, Mainz; Jeff Schell, Köln, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 08/903,325

(22) Filed: Jul. 17, 1997

Related U.S. Application Data

(63) Continuation of application No. 08/383,747, filed on Feb. 2, 1995, now abandoned, which is a continuation-in-part of application No. 08/235,106, filed on Apr. 28, 1994, now abandoned, which is a continuation of application No. 07/766,990, filed on Sep. 27, 1991, now abandoned.

(30) Foreign Application Priority Data

Oct. 6, 1990 (DE) ................................. 40 31 758

(51) Int. Cl.[7] ........................... C12N 15/29; C12N 15/56; C12N 15/82; A01H 5/00

(52) U.S. Cl. ...................... 800/205; 536/23.2; 536/23.6; 536/24.1; 536/24.3; 435/172.3; 435/320.1; 435/252.3; 435/419; 435/200; 435/69.1; 800/250

(58) Field of Search ................................. 536/23.2, 23.6, 536/24.1, 24.3; 435/172.3, 320.1, 252.3, 419, 200, 69.1; 800/205, 250

(56) References Cited

U.S. PATENT DOCUMENTS 4,940,840 * 7/1990 Suslow et al. ....................... 800/205

FOREIGN PATENT DOCUMENTS

| 0298918 | 2/1989 | (EP) . |
| 0309862 | 4/1989 | (EP) . |
| 3922225 | 10/1990 | (EP) . |
| 9007001 | * 6/1990 | (WO) . |

OTHER PUBLICATIONS

Broglie et al 1986 Proc Natl Acad Sci USA 83:6820–6824.*
Shinshi et al 1987 Proc Natl Acad Sci USA 84:89–93.*
Gaynor et al 1988 Nucleic Acids Research 16(11):5210.*
Gaynor et al 1989 Nucleic Acids Research 17(14):5855–5856.*
Payne et al 1990 (Jan.) Proc Natl Acad Sci USA 87:98–102.*
Shinshi et al 1990 (Mar.) Plant Molec Biol 14:357–368.*
Samac et al 1990 (Jul.) Plant Physiol 93:907–914.*
Flach et al 1992 Experientia 48:701–716.*
Neuhaus et al 1991 (Jan.) Plant Molec Biol 16:141–151.*
Oppenheim et al 1992 Trends in Biotechnology 10:392–394.*
Thomas Herget et al., "Elictor–specific induction of one-member of the chitinase gene family in *Arachis hypogaea*", Mol. Gen. Genet., 224, pp. 469–476 (1990).

Molecular Plant–Microbe Interactions, vol. 3, No. 4, 1990, pp. 255–258; Linthort, H.J.M., et al.: "Analysts of Acidic and Basic Chitinases from Tobacco and Petunia and Their Constitutive Expression in Transgenic Tobacco", p. 254.

Mol. Gen. Genet, vol. 224, No. 3, Dec. 1990, pp. 469–476; Herget, T., et al.: "Elicitor–Specific Induction of One of the Chitinase Gene Family of Arachis Hypogaea".

Biological Abstracts BR40:19947, Annual Meeting of the American Phytopathological Society and the Canadian Phytopatholpogical Society and the Canadian Phytopathological Soceity, Aug. 4–8, 1990, vol. 80, No. 10, 1990, p. 1067, Woloshuk, C.P., et al.: "Antifungal Activity of Chitinases Expressed in Transgenic Tobacco".

Chemical Abstracts, vol. 108, columbus, Ohio, US; Abstract No. 128682q, Hedrick, S.A., et al.: "Chitinase cDNA Cloning and mRNA Introduction by Fungal Elicitor, Wounding, and Infection" & Plant Physiology, vol. 86, No. 1, 1988, Rockville, MD, USA, pp. 182–186.

Samac et al 1990 Plant Physiol 93:907 914.

Hideaki Shinshi, et al., Plant Molecular Biology, 14:357–368, 1990, "Structure of a tobacco endochitinase gene: evidence that different chitinase genes can arise by transposition of sequences encoding a cysteine–rich domain".

Thomas Herget, et al., Mol. Gen. Genet (1990) 224:469–476 Elicitor–specific induction of one member of the chitinase gene family in *Arachis hypogaea*.

Karen E. Broglie, et al., Prac. Natl. Acad. Sci. USA, vol. 83, pp. 6820–6824, Sep. 1986, Botany, Ethylene–regulated gene expression: Molecular cloning of the genes encoding an endochitinase from *Phaseolus vulgaris*.

Karen E. Broglie, et al., The Plant Cell, vol. 1, 599–607, Jun. 1989 American Society of Plant Physiologists, Functional Analysis of DNA Sequences Responsible for Ethylene Regulation of a Bean Chitinase Gene in Transgenic Tobacco.

John J. Gaynor, Nucleic Acids Research, vol. 16, No. 11, 1988, "Primary structure of an endochitinase mRNA from *Solanum tuberosum*".

John J. Gaynor, et al., Nucleic Acids Research, vol. 17, No. 14, 1989, Sequence analysis of a genomic clone encoding an endochitinase from *Solanum tuberosum*.

Susan A. Hedrick, et al., Plant Physiol. (1988) 86, 0182–0186, "Chitinase cDNA Cloning and mRNA Induction by Fungal Elicitor, Wounding, and Infection".

(List continued on next page.)

Primary Examiner—Douglas W. Robinson
Assistant Examiner—Thomas Haas
(74) Attorney, Agent, or Firm—Sprung Kramer Schaefer & Briscoe

(57) ABSTRACT

The present invention relates to DNA isolated from *Arachis hypogaea* which encodes or hybridizes to DNA which encodes a protein that repels pests. Such DNA is useful in the transformation of vectors, host organisms and plants and for the production of plants which exhibit an increased resistance to pests.

20 Claims, 3 Drawing Sheets

OTHER PUBLICATIONS

Michel Legrand, et al., Proc. Natl. Acad. Sci. USA, vol. 84, pp. 6750–6754, Oct. 1987, Botany, "Biological function of pathogenesis–related proteins: Four tobacco pathogenesis–related proteins are chitinases".

George Payne, et al., Proc. Natl. Acad. Sci. USA, vol. 87, pp. 98–102, Jan. 1990, Biochemistry, "Isolation of complementary DNA clones encoding pathogenesis–related proteins P and Q, two acidic chitinases from tobacco".

C. H. Rolfs, et al., Plant Cell Reports (1981)1:83–85, Cultured Cells of *Arachis Hypogaea* Susceptible to Induction of Stilbene Synthase (Resveratrol–forming).

Angela Schlumbaum, et al., Letters to Nature, vol. 324, Nov. 27, 1986, Plant chitinases are potent inhibitors of fungal growth.

Hideaki Shinshi, et al., Proc. Natl. Acad. Sci. USA, vol. 84, pp. 89–93, Jan. 1987, Botany, "Regulation of a plant pathogenesis–related enzyme: Inhibition of chitinase and chitinase mRNA accumulation in cultured tobacco tissues by auxin and cytokinin".

John P. Carr, et al., Prac. Natl. Acad. Sci, USA, vol. 82, pp. 7999–8003, Dec. 1985, Biochemistry, "Synthesis of pathogenesis–related proteins in tobacco is regulated at the level of mRNA accumulation and occurs on membrane–bound polysomes".

Juergen Ebel, et al., TIBS 13—Jan. 1988, "Defense strategies of soybean against the fungus *Phytophthora megasperma f.sp. glycinea:* a molecular analysis".

Christian C. Fritz, et al., Proc. Natl. Acad. Sci, USA, vol. 88, pp. 4458–4462, May 1991, Biochemistry, Reduced steady–state levels of rbcS mRNA in plants kept in the dark are due to differential degradation.

Finnegal et al, 1994, Bio/Technology 12:883–887.

Keith et al, 1986, EMBO J. 5:2419–2425.

Larkins et al, 1985, J.Cell Biochem Suppl. O ((PAKTC): 264.

Lewin, R., 1987, Science 137:1570.

Reeck et al, 1987, 611 50:667.

Bowie et al, 1990, Science 247: 1306–1310.

Flach et al, 1992 Experientia 48:701–716.

Neuhaus et al (1991 (Jan.) Plant Molec.Biol. 16:141–151.

Oppenheim et al (1992) Trends in Biotechnology 10:392–394.

* cited by examiner

```
Positions   1-1169 Promotor
Position         1126 a Transcription start site
            1170-1636 Exon I: coding part
            1637-2555 Intron I;
            2556-2922 exon II: coding part
            2923-end 3'-untranslated region 1 ATCGATACCA TGTGTCCATA TTTTTATACT TTTAGCCTCA AATTCTTTCA
  51 TTTCTTAAGA GTATAAAGAC ATAATATTAT CTATCAACCT ATTATATTAT
 101 TATTAGGGTG GCATGTATGC ATAGGTTCTA TGGCTAGTCT CGTATTTATT
 151 CAAAGGTGAA TTTTAACAAA ACTATGAATG GTATAGTTTT TAAATGGGTT
 201 TATAAGTGTT AGTCATTCCT CGCTTTTTGA ATTAGTTTTT TGAATTGAGG
 251 TAGACTCGTT CAAACTCAAT TTTAATATAA GAAAAAAAAT ATTAAGGATG
 301 TTACAAATAA AAATTTTAAT AAACAATATT ACTTTTTAAA AATTTTCAAT
 351 ACAATAAAAT GTATGGAAAA ATGCTAAAAC TTTTTATTTT ACCTTCGTTA
 401 ACTAATGCCG AAAGTCCAAT CCCATTTTCC TCCATTCATG GACTATGTCA
 451 ATGTGACATG ATAATGATGG TTATCAAGAA CTCAAATTTT AGTACAACTG
 501 GTATAAAAAA ATATTGAAAG TAATAGATAG ATTTGAGAAG TGAAATCAAA
 551 TTATACATGA ATTGAAGAAT GACTCTGAAA CATCTTATTA ATCTCTTCCA
 601 CCTCCACAAT GATATCACAC ACTCCAATTC ATAAATAAAA ACATAATTTT
 651 TTATGCATCT TTTAATAATT TCAAAGTCTT ATGTTTAAGA TAGGAGGGCA
 701 AAGATAACAA CAATATATGA TGGAAGCTTC AGAAAGTCAA AACTAGTTTA
 751 GTCATCATTT TATATAAACT TGGAATGGTC CTCTCAATTA AATATGAGAG
 801 AAGGATTCAA AGCCGAAAAC ATTTCTTTAA TTTTCATTCA AGTTCTCTAT
 851 TATGTTACAA ATTTAGTATC AACAAATTAA TAACAAAGAA ATACATTATG
 901 AAGCAGCTTG CCAAGTAGGA ACACACTAAA TGGGTTTCAT AATAAATGAT
 951 GAACATATAA TGCGTTAGTG AGTAGGACAA CATAAACCGT TGACCTTTGA
1001 CCCTCCACGC CCACTAAGCC ACCACCGTCT TTTACCTTTG AATATACGAA
1051 ATCTTTGTGT AGCGTTGAGT ATTGATTATT GAAATTGTAC ATATATAAAC
```

Fig. 1-a

```
1101  CTTAATCCTA CCTCATATCA TTCCCACATA AAAACCAAAC CAATCCTTGA
1151  TAACATAACA TCCAATAAC
                              A TGGCATTATT CTCATTCTCA TTCTCCTCAT
1201  TCTGCCTCAC AATTTTTGTC ATCTATTCTT CTTTATCTCT ATCTGCTGAA
1251  TCACGTGTCT CACCAATTGC ACCAATCTCT TCTCTCATTA GCAAAACCCT
1301  TTTCGACTCA ATCTTTTTAC ATAAAGATGA CAATGCTTGC CCTGCTAGAA
1351  ACTTTTACAC TTATGAATCC TTCGTTGAGG CAACCTCGAG CTTCCCAGCG
1401  TTCGGCTCGA CCGGATGCTC GGCCACACGG AAGCGCGAGG TTGCCGCATT
1451  TCTTGCACAG ATCTCACATG AAACCACAGG TGGTTGGGCT ACTGCACCTG
1501  ATGGACCATA TGCTTGGGGG CTGTGCTTCA AGGAAGAAGT TAGTCCTCAA
1551  AGTGATTATT GTGATTCCTC CAACAAAGAA TGGCCCTGTT ATCCTGGAAA
1601  GAGTTACAAA GGCAGAGGAC CAATTCAACT TTCCTG
                                          GTAT ATAATATATA
1651  AATCTTTCAT ATTTGCATGT TTTTACATCC ATTATATTAT TTGCACTCCA
1701  AGAAAGTTAT GGTCCATTTA CATACTAACT CTTCTCCTGT GAGATTAGAT
1751  TGTGGATTTT TCTCATTTTG CATTCATCTA ATTTTTTTTT CATGTTTAAG
1801  TATGATAAGT ATATATGCAG TTGAATTATC AATTATATTA GTAATTAAGT
1851  TTCTTTTCAT CTTGTTTGCG ATACTGTGTT CAACTCACTA ATAAATGCCA
1901  ATTTAATAGA CAAACAACAT TTTTGTTTCT ATATTATTAT TTTGACTAAA
1951  GATGTTTACT TAATATGACC TTGTCTTCTT TAATTATAAT TAGTGAAAAT
2001  ATCAAATCTC TCAAATTATT TAATAATTTC TAACTATCAA TTTCACATAA
2051  AATTAATTGT ACTTGAGTTT CTACCTTTTT AAATAGTACT AAAAAAATAA
2101  AAATAATATT TACTAATCGT ACTGAATTCT TAAAAAAGA AACACAATAT
2151  GATGTGCATT TTTAATTAAA TATTGAATTT AATTTTTATA TATTATTAGT
2201  ATAAAATTTT TTACACATAA TTAATTGTGT ATTGTTATAT CAATAGAAAT
2251  AATTAATTTT TACATTGTTA GTATATTAAA ATTAAAAAAT TATCTAAATA
```

Fig. 1-b

```
2301  TATAAATATT ATCAAATAAT CTATTTACAT TATTAGTGTC TCAAAATTAA
2351  AATCCTCATA TATTTATTTT TTAATTCATG ACAAAAAAAA GACATGTGAA
2401  TAAAACTCTA CTATATTCTT AGGGGATTGG ATGTCCACAA CTAATATGCC
2451  ATTTGTGCCA AGTCTCAGCT GCCTGCTTGC GTGATTGTTT AGATTATTCA
2501  AATGTGAAAG CCAATTGTTG CATGGATGTA CTTACTCTTT CTTTTTTTGT
2551  GTTAG
              GAATT ACAACTATGG GCCAGCAGGG AAGGCCTTGG GATTCGATGG
2601  CCTTAAGAAC CCAGACATTG TGTCAAACAA TTCAGTAATT GCATTCAAAA
2651  CAGCACTCTG GTTTTGGATG ACAGAGCAGA AACCAAAACC TTCTTGCCAC
2701  AACGTCATGG TTGGGAATTA CGTGCCAACA GCATCTGATA GAGCAGCAAA
2751  TAGAACCTTA GGGTTTGGGT TGGTTACTAA CATAATCAAC GGTGGACTTG
2801  AATGTGGAGT TCCAGATGAT GCAAGAGTCA ATGATCGGAT TGGATACTTT
2851  CAAAGATATG CTAAGTTGTT TAATGTAGAT ACTGGACCTA ACTTGGATTG
2901  TGCATATCAG AAATCCTTCT AA
                              GCTTACAT TGTTTTTGGT GTATCCTTTC
2951  TTTTTCTTTT GTTTCTATAA TTTTCTCTAT TTAGTAAATG GTCAAATTCA
3001  TTTTTAAAAG ATTATTTATG TTTAAATTGA TCTTCGAAAG ATTATTCAGC
3051  TTTTAAAAAT TTTAAATTGG TCACATTAAT CCCTCTGTCA CTTTCATTTT
3101  TCGTGGCATC AAAATTTGTT GATATGACAC TTTAAGTGAC ACTACAACAG
3151  ATATCTGACA ATTCTAATTA GGTGCTAATA TGATAAATTT ATGAAATTAG
3201  ACCAAATCAA TCCTAATTTG AAAATTTTCA ATGTCTCAAA ATCTTGTTGA
3251  AGTTAGGGTT GATTTCATCT AATTGCATAA ATTTAGTATG TTAACAATCA
3301  ATTAGGACAG CTAGGAATAT ACTATGGTCA ATATGGTGTC ACTTCGTCAA
3351  CAATGAAAAT GACAAAATGA CTAATATAAC TAATTTAAAA TATTTGAAAA
3401  ATAAATTTGA TT
```

Fig. 1-c

RESISTANCE GENES

This application is a continuation of application Ser. No. 08/383,747, filed Feb. 2, 1995, now abandoned, which is a CIP of Ser. No. 08/235,106 filed Apr. 28, 1994, now abandoned, which is a continuation of Ser. No. 07/766,990 filed Sep. 27, 1991, abandoned.

BACKGROUND OF THE INVENTION

1. Field of the Invention

The present invention relates to new resistance genes which have been isolated from plants and to their use for the, transformation of vectors, host organisms and plants, and to the production of plants which exhibit an increased resistance to pests.

2. Description of the Related Art

Many plants are provided with natural possibilities for resisting pests. These resistance mechanisms are controlled by resistance genes. They can be activated by biotic stimuli (for example attack by pests) or abiotic stimuli (for example UV light). In most cases, the mechanisms of these resistances are not yet fully known. There is a demand for having resistance genes available which are primarily activated by pests and which can be incorporated into the genome of plants to further increase the latter's already existing resistance to pests. Such resistance genes which can specifically be induced by pests were hitherto unknown.

SUMMARY OF THE INVENTION

New resistance genes have now been isolated from plants, and these resistance genes can be incorporated into the hereditary matter (the genome) of plants which produce no, or insufficient amounts of, repellent substances, or produce the latter at too late a point in time, it being possible in this manner to bring about increased resistance of these plants to pests (pathogens).

The new resistance genes are characterised in that they can be specifically induced by pathogens and in that they contain DNA sequences which correspond to the cDNA of the following sequence:

```
1                                                    50
ATCTCGTTCA AGTCGGCGCT CTGGTTGTGG ATGACAGAGC AGAAACCAAA 51                                                  100
ACCTTCTTGC CACAACGTCA TGGTTGGGAA TTACGTGCCA ACAGCATCTG 101                                                 150
ATAGAGCAGC AAATAGAACC TTAGGGTTTG GGTTGGTTAC GAACATCATC 151             170
AACGGCGGCC TGGACTGCGG
```

It is surprising that a new type of resistance genes could be found which contain sequences which correspond completely, or essentially, to the abovementioned cDNA. This cDNA sequence is novel, and its existence could not have been anticipated.

Furthermore, it must be regarded as surprising that the new resistance genes are essentially activated by pathogens (pests) or by cell-wall fragments of pathogens (elicitors), while other, conventional biotic and abiotic inductors have no substantial effect. The new resistance genes are therefore highly suitable for increasing resistances to pests in transgenic plants.

BRIEF DESCRIPTION OF THE DRAWINGS

FIGS. 1a, 1b and 1c collectively depict the sequence of genomic clone λchit2a.

DESCRIPTION OF THE PREFERRED EMBODIMENTS

Resistance genes which contain DNA sequences which correspond to the abovementioned cDNA contain DNA sequences which are complementary to the cDNA and which, after having been transcribed into mRNA and this mRNA having been used as a template, can produce the cDNA mentioned. Resistance genes according to the invention are genes whose expression is specifically inducible by pathogens and which hybridise with the above-mentioned cDNA.

Resistance genes are understood as meaning nucleic acids (DNA) which, in plants, cause the formation of substances which are suitable for repelling or destroying pests which attack the plants, or which prevent these pests from spreading. These substances are preferably enzymes and, in particular, hydrolases, preferred hydrolases being those which can cleave β(1–4) bonds in N-acetyl-D-glucosamine polymers, or polymers which contain N-acetyl-D-glucosamine (chitinases).

These nucleic acids can exist in a form in which they are isolated from their natural environment (plants) or in which they are integrated in a vector, for example in plasmids, phages or cosmids, or they can be contained in a prokaryotic DNA, for example bacterial DNA, or eukaryotic DNA, for example plant DNA, as "foreign" DNA or as "additional" DNA.

Resistance genes are also understood as meaning those resistance genes which additionally contain, at their beginning and/or end, DNA sequences which do not interfere with the function of the genes, or not to a considerable extent. These DNA sequences, which are also termed "gene units", are formed for example by cutting out with restriction enzymes, for example with BamHl, XbaI or HindIII, by cleaving the genomic DNA as it is obtained, for example, by extracting from the *Arachis hypogaea* suspension cell line (Rolfs, Fritzemeier, Kindl (1981).

The resistance genes (or the gene units) can exist in the form in which they are contained in the genome of plants ("genomic" form, including non-encoding sequences (such as introns)),or in a form which corresponds to the cDNA ("copy" DNA) which can be obtained via mRNA with the aid of reverse transcriptase/polymerase (and no longer contains introns). The resistance genes can also exist in partly synthetic, or completely synthetic, form.

In the resistance genes (or the gene units) according to the invention, DNA sequences can be replaced by other DNA sequences or DNAs which essentially act in the same fashion, as long as this does not adversely affect, or prevent, the formation of essentially functional repellent substances.

It is also possible for them to carry, at the ends, those DNA sequences which are adapted in each case to the handling of the genes (or the gene units) (for example "linkers").

In the present connection, "foreign" DNA is understood as meaning such DNA which does not naturally occur in a particular prokaryotic or eukaryotic genome but which is only incorporated into this genome as a result of manipulation by man. "Additional" DNA will be such DNA which does in fact occur naturally in the particular prokaryotic or eukaryotic genome, but is only incorporated into this genome in an additional amount as a result of manipulation by man. One or more specimens of the "foreign" DNA or "additional" DNA can be incorporated, depending on the requirement and the nature of the case in question.

As already mentioned, resistance genes are preferably understood as meaning those genes which produce hydrolases, chitinase-type hydrolases being particularly preferred.

The resistance genes according to the invention are derived from monocotyledon and dicotyledon plants. Preferred resistance genes according to the invention are those which can be isolated from dicotyledon plants, in particular Solanaceae and Leguminosae and, particularly preferably, from groundnut,(Arachis hypogaea). Using the abovementioned cDNA as a probe, plants can be examined for the presence of the resistance genes by customary methods.

Resistance genes which are particularly preferred according to the invention are those resistance genes which contain DNA sequences which correspond to the abovementioned cDNA sequence and which can be induced by pathogens (in particular fungi or fragments of fungal cell walls), preferably by *Phytophthora megasperma* or its cell wall fragments, and, amongst these, in particular those which can be isolated from *Arachis hypogaea* (groundnut).

These genes, or essential portions thereon, are located on 3 DNA fragments of approx. 2 to 3 kbp (in the case of cleavage with HindIII) or on fragments between approx. 5 and approx. 23 kbp (in the case of cleavage with XbaI or BamHI).

The resistance genes according to the invention can be located, isolated, purified and detected in plants, for example groundnut, with the aid of the generally customary and known processes and methods in molecular biology, using the following cDNA sequence as a probe:

plant. With the aid of plaque hybridisation, the resistance genes in the corresponding vector are isolated with the aid of the cDNA. The nucleic acids obtained from the isolates are used for direct transformation of plants. It is also possible to isolate the desired gene from the isolates with the aid of the customary methods and to employ it in other transformation methods, for example with the aid of *Agrobacterium tumefaciens*.

In general, the resistance genes which are isolated with the aid of the abovementioned cDNA are specifically inducible by pathogens. However, cases are feasible in which, depending on the nature of the plant, the signal chain required for induction is non-functional or non-existent. The indication of resistance can be checked by incubating plants, or parts of plants, with a pathogen, or with its cell wall fragments. The specific inducibility can be detected using the customary methods (for example Northern analysis) and with the aid of the abovementioned cDNA.

By way of example, this method will be illustrated in the case of the groundnut resistance genes, as follows:

Deoxyribonucleic acid DNA is isolated from the *Arachis hypogaea* suspension cell line (Rolfs et al. 1981), and one aliquot in each case is cleaved with a restriction endonuclease, preferably with the enzymes HindIII or MboI. The DNA is then separated with the aid of sedimentation centrifugation or with the aid of gel electrophoresis, according to its fragment size (Sambrook, Fritsch and Maniatis, 1989). The fractions which contain fragments of a size of up to approx. 10 kb (HindIII), or of approx. 10–20 kb (MboI), are cloned into the lambda vectors (lambda ZAP II or lambda FIX II; Stratagen GmbH, Heidelberg).

In this manner, parts of a gene library of groundnut are established which contain resistance genes in the sense of the invention. Vectors which contain these resistance genes can be identified unequivocally with the aid of the cDNA probe which is cloned into pR 3-7, and purified further. The purified nucleic acid which contains the resistance genes is then transferred to tobacco or other plants with the aid of the direct DNA transformation or other transformation methods, preferably by *Agrobacterium tumefacions*.

An analogous procedure can be applied to the isolation of the resistance genes from other plants.

```
1                                                          50
ATCTCGTTCA AGTCGGCGCT CTGGTTGTGG ATGACAGAGC AGAAACCAAA 51                                                        100
ACCTTCTTGC CACAACGTCA TGGTTGGGAA TTACGTGCCA ACAGCATCTG 101                                                       150
ATAGAGCAGC AAATAGAACC TTAGGGTTTG GGTTGGTTAC GAACATCATC 151               170
AACGGCGGCC TGGACTGCGG
```

For this purpose, the DNA of the plant in question is isolated, and useful restriction endonucleases are determined with the aid of the Southern blot technique (preferably those which give fragments of uniform size, where the size of the fragments with which this DNA is digested should not be less than 2 kb and more than 28 kb). The fragments obtained are separated according to their size. Fragments which hybridise with the abovementioned cDNA are cloned in suitable vectors as a partial gene library of the particular The abovementioned cDNA sequence, including the DNA sequences which act essentially in the same fashion (in which the applicability as a probe is retained), is part of the present invention. It can be obtained by the known methods of DNA synthesis, or can be obtained from plasmid PR 3-7 in the customary manner, by digesting with EcoRI or HindIII, followed by isolation of a fragment of approx. 170 kb. Another part of the present invention are DNA sequences which correspond to this cDNA, that is to say, which can also contain, for example, non-encoding DNA sequences (introns), and the sequences which act in essentially the same fashion.

Plasmid pR 3-7 consists of the starting plasmid pUC 19, into whose cleavage sites the cDNA mentioned has been cloned via smooth ends. The cDNA can be cut out completely, for example using EcoRI and HindIII, the cDNA being flanked at the 5'-end (Pos-1) and Et the 3'-end by the sequences which can be seen below (flanking ends in lower-case letters):

```
1
gaattcgagc tcggtacccg gggatcctct agagtcATCT CGTTCAAGTC

51
GGCGCTCTGG TTGTGGATGA GAGAGCAGAA ACCAAAACCT TCTTGCCACA

101
ACGTCATGGT TGGGAATTAC GTGCCAACAG CATCTGATAG AGCAGCAAAT

151
AGAACCTTAG GGTTTGGGTT GGTTACGAAC ATCATCAACG GCGGCCTGGA

201
CTGCGGgacc tgcaggcatg caagctt
```

This DNA sequence is part of the present invention. It can be used directly as a probe (as in the case of the cDNA) for locating genes according to the invention. If it is desired to obtain the cDNA sequence without flanking sequences, it can be produced synthetically, both with the aid of PCR reaction (polymerase chain reaction) and the synthetic oligonucleotides $5'$ ATC TCG TTC AAG TCG GCGCT$^{3'}$ and $5'$ CCG CAG TCC AGG GCG; CCGTT$^{3'}$, or, alternatively, completely synthetically.

The strain *Escherichia coli* RG-2, which contains plasmid pR 3-7, was deposited at the Deutsche Sammlung von Mikroorganismen [German Collection of Microorganisms] (DSM), Mascheroder Weg 1b, D-3300 Braunschweig, Federal Republic of Germany, in agreement with the regulations of the Budapest Treaty on the International Recognition of the Deposit of Microorganisms for the Purposes of Patent Procedures (date of deposit: Aug. 28, 1990), and it has the deposit number DSM 6149.

This strain (*E. coli* K12) as well as its mutants which contain the plasmid, are also part of the present invention.

The required amounts of cDNA (if appropriate with flanking sequences) can be obtained readily in a known fashion by multiplying the strain, followed by isolation, by the known methods.

The resistance genes from plants according to the invention can be specifically induced by pathogens and contain DNA sequences which correspond to the above-identified cDNA. This means that homology of different degree exists between the DNA sequences and the cDNA, this homology being sufficient to allow the isolation of the resistance gene with the above-mentioned cDNA as a probe.

Therefore, the present invention refers to such resistance genes from plants which are specifically induced by pathogens and can be isolated by using the above-mentioned cDNA as a probe.

Functionally complete genes, like the resistance genes according to the invention, consist of regulatory portions (in particular the promoter) and the structural gene which encodes for the protein in question.

Both gene portions can be used independently of one another. For example, it is possible to arrange downstream of the regulatory portion a different DNA sequence (which deviates from the resistance gene), which is intended to be expressed after being incorporated into the plant genome. Since only few isolated promoters are known and no promoters have hitherto been available which can be activated specifically by pathogens and which can become active in plants, the promoters of the resistance genes according to the invention, which are also part of the present invention, constitute valuable tools in the production of transgenic plants which have an increased resistance to pathogens.

Equally, it is possible to arrange a "foreign" regulatory portion upstream of the structural resistance genes. This might be of advantage when, in particular plants, only certain regulatory genes (for example autologous plant genes) can become active to a sufficient extent. The structural resistance genes as well as DNA of the abovementioned sequence (cDNA) therefore represent valuable units which can be employed on their own, and, as already explained, are equally part of the present invention. The resistance genes according to the invention can be separated into the regulatory portions and the structural genes by the customary methods. It is preferred to use the complete resistance genes (or the gene units) according to the invention.

With the aid of the customary methods, it is possible to incorporate the resistance genes (or the gene units) or portions thereof, in one or more copies (for example tandem arrangement), preferably in one copy, into any prokaryotic (preferably bacterial) or eukaryotic (preferably plant) DNA as "foreign" or "additional" DNA. The recombinant DNA which has been "modified" in this way and which can be used, for example, for transforming plants or plant cells, and which, after transformation, is contained in plants or plant cells, is a component of the present invention.

The resistance genes (or the gene units) and/or portions thereof, the cDNA with the abovementioned sequence and the genomic DNA which corresponds o this cDNA, as well as the modified DNA, can be contained in vectors (in particular plasmids, cosmids or phages), in transformed microorganisms (preferably bacteria, in particular gram-negative bacteria such as *E. coli*) as well as in transgenic plant cells and plants, or in the DNA thereof, as "foreign" or "additional" DNA. Such vectors, transformed microorganisms (which can also contain these vectors) as well as the transgenic plant cells and plants and the DNA thereof represent components of the present invention.

Pests against which resistances, or increased resistances, can be obtained with the aid of the resistance genes according to the invention are preferably pests which can be prevented from damaging the plants by hydrolases, in particular of the chitinase type. Pests which may preferably be mentioned are arthropods such as insects and mites, nematodes as well as microbial pests such as phytopathogenic fungi and bacteria. Microbial pests, in particular phytopathogenic fungi, are particularly emphasised.

The harmful insects in particular include insects from the order of the:

Orthoptera, Dermaptera, Isoptera, Thysanoptera, Heteroptera, Homoptera, Lepidoptera, Coleoptera, Hymenoptera and Diptera.

The harmful mites include, in particular:

Tarsonemus spp., Panonychus spp. and Tetranychus spp.

The harmful nematodes include, in particular:

Pratylenchus spp., Heterodera spp. and Meloidogyne spp.

The microbial pests include, in particular, the phytopathogenic fungi:

Plasmodiophoromycetes, Oomycetes, Chytridiomycetes, Zygomycetes, Ascomycetes, Basidiomycetes, Deuteromycetes.

The phytopathogenic bacteria include, in particular, the Pseudomonadaceae, Rhizobiaceae, Enterobacteriaceae, Corynebacteriaceae and Streptomycetaceae.

Some causative organisms of fungal and bacterial diseases which come under the generic names listed above may be mentioned as examples, but not by way of limitation:

Xanthomonas species, such as, for example, *Xanthomonas campestris* pv. *oryzae;*

Pseudomonas species, such as, for example, *Pseudomonas syringae* pv. *lachrymans;*

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubense;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae;*

Pseudocercosporella species, such as, for example, *Pseudocerco sporella herpotrichoides. Helminthosporium carbonum* may also be listed.

The plants to which resistance, or increased resistance, to the above pests can be imparted by incorporation (transformation) of the resistance genes (or the gene units according to the invention include virtually all plants. Particular demand for the provision of resistance is naturally in crop plants, such as forest plants, for example firs, spruces, Douglas firs, pines, larches, beeches and oaks, as well as plants which provide food and raw materials, for example cereals (in particular wheat, rye, barley, oats, millet, rice and maize), potatoes, legumes such as pulses and, in particular, alfalfa, soya beans, vegetables (in particular cabbage species and tomatoes), fruit (in particular apples, pears, cherries, grapes, citrus fruits, pineapples and bananas), oil palms, tea shrubs, cocoa shrubs and coffee shrubs, tobacco, sisal and cotton, as well as in medicinal plants, such as Rauwolfia and Digitalis. Crop plants which may be mentioned as particularly preferred are potatoes, tomatoes, grape-vines and legumes. It is preferred to incorporate the resistance genes according to the invention into the genome of plants in the form of "foreign" DNA.

As already mentioned, one or more copies of the resistance genes (or the gene units) according to the invention are incorporated into the natural plant genome (at identical or different sites of the genome), preferably into the nuclear genome, it also being possible for different resistance genes to be combined with each other.

In the case of plants which already carry resistance genes according to the invention, the incorporation of one or more resistance genes according to the invention can lead to a considerably improved resistance behaviour. If appropriate, only the structural genes according to the invention are used, and upstream incorporation of a regulatory DNA element isolated from the respective plant may be possible.

The increased resistance of the transformed plant cells and plants according to the invention is important for agriculture and forestry, for the cultivation of ornamental plants and medicinal plants, and for plant breeding.

The invention therefore also relates to a method of producing transgenic plant cells (including protoplasts) and plants (including parts of plants, and seeds) having an increased resistance to pests, which method is characterised in that (a) one or more resistance genes (or gene units) according to the invention and/or portions of the resistance genes (or of the gene units) and/or recombinant DNA which has been modified according to the invention are incorporated into the genome of plant cells (including protoplasts) and, if appropriate, (b) complete transformed plants are regenerated from the transformed plant cells (including protoplasts having an increased resistance to pests, and, if appropriate, (c) the desired parts of the plants (including seeds) are obtained from the resulting transformed plants of the parental generation or of further generations derived therefrom.

Process steps (a), (b) and (c) can be carried out in the customary manner by known processes and methods.

Transgenic plant cells (including protoplasts) and plants (including parts of plants, and seeds) which contain one or more resistance genes (or gene units) according to the invention and/or portions of the resistance genes (or of the gene units) as "foreign" or "additional" DNA, as well as those transgenic plant cells and plants which can be obtained by the above processes, are equally part of the present invention.

Parts of the present invention are also the:

(a) use of the resistance genes (or of the gene units) according to the invention and/or portions thereof and/or the DNA modified according to the invention and/or the vectors according to the invention and/or the transformed microorganisms according to the invention, for the production of transgenic plant cells (including protoplasts) and plants (including parts of plants, and seeds), as well as the (b) use of the transgenic plant cells (including protoplasts) and plants (including parts of plants, and seeds) according to the invention for the production of propagation material and for producing novel transgenic plants and propagation material thereof, and, generally, the (c) use of the resistance genes (or of the gene units) according to the invention and/or portions thereof and/or the DNA modified according to the invention in transgenic plants for combating pests.

A number of various methods are available for incorporating the resistance genes, or the gene units or portions thereof, into the genetic material of plants or plant cells in the form of "foreign" or "additional" DNA. The gene transfer can be carried out following the generally customary known methods, it being possible for a person skilled in the art to determine the method which is suitable in each case without difficulty.

A particularly favourable vector which can be employed in many species and which is available for transferring foreign DNA into genomes of dicotyledon and monocotyledon, preferably dicotyledon, plants is the Ti plasmid of *Agrobacterium tumefaciens*. The resistance genes or portions thereof are introduced into the T-DNA of suitable Ti plasmids (for example Zambryski et al. 1983) and transferred by infecting the plant, infecting parts of plants or plant tissues such as, for example, leaf discs, stalks, hypocotyls, cotyledons, meristems and tissues derived from these such as, for example, secondary embryos and calli, or by coculturing protoplasts with *Agrobacterium tumefaciens*.

An alternative is the incubation of purified DNA containing the desired gene in plant protoplasts (for example Hain et al., 1985; Krens et al., 1982; Paszkowski et al., 1984) in the presence of polycations or calcium salts and polyethylene glycol.

DNA uptake can also additionally be enhanced by an electrical field (electroporation) (for example Fromm et al., 1986).

The DNA can also be incorporated in a known manner using plant pollen, by "bombarding" pollen with physically accelerated particles which carry the DNA (cf. EP-A 0,270, 356).

The plants are regenerated in a known manner with the aid of suitable nutrient media (for example Nagy and Maliga 1976).

In a preferred embodiment of the method according to the invention (in accordance with the method described in EP-A 116,718), the genes or gene units according to the invention are cloned into a suitable intermediary *E. coli* vector, for example pGV700 or pGV710 (cf. EP-A-116,718; Deblaere et al. 1986), or, preferably, derivatives thereof which additionally contain a reporter gene such as, for example, nptII (Herrera-Estrella et al. 1983) or hpt (Van den Elzen et al 1986).

*Escherichia coli* strain AZ 4, which contains the vector pGV 710 in a form in which it can be readily isolated, was deposited at the Deutsche Sammlung von Mikroorganismen [German Collection of Microorganisms] (DSM), Grisebachstraße 8, D-3400 Göttingen, Federal Republic of Germany, in agreement with the regulations of the Budapest Treaty on the International Recognition of the Deposit of Microorganisms for the Purposes of Patent Procedures, and has the deposit number DSM 3164.

The plasmid of the above construction is transferred to *Agrobacterium tumefaciens* which contains, for example, pGV 3850 or derivatives thereof (Zambryski et al. 1983) using customary methods (for example Van Haute et al. 1983). Alternatively, it is possible to clone the resistance gene unit in a binary vector (for example Koncz and Schell 1986) and transfer it into a suitable agrobacterium strain as described above (Koncz and Schell 1986). The resulting agrobacterium strain which contains the resistance gene unit in a form which can be transferred to plants, is subsequently used for plant transformation.

In a further preferred embodiment, a suitable plasmid with the resistance gene, if appropriate together with another plasmid which contains a reporter gene for plant cells, for example for kanamycin resistance (for example Herrera-Estrella et al. 1983) or a hydromycin resistance (van den Elzen, 1986), preferably pLGV neo 2103 (Hain et al. 1985), pLGV 23 neo (Herrera-Estrella 1983), pMON 129 (Frayley R. T. et al., (1983)), pAK 1003, pAK 2004 (Velten J. et al. (1984)) or pGSST neo 3 (pGSST3) (EP-A-189,707), is transferred to plant: protoplasts in a customary manner by direct gene transfer (for example Hain et al. 1985). In this context, the plasmid, or plasmids, can exist in circular, but preferably in linear, form. When a plasmid with a reporter gene is used, kanamycin-resistant protoplasts are then checked for expression of resistance factors. In the other case (without reporter gene), the resulting calli are tested for the expression of the resistance gene (screening by customary methods).

Transformed (transgenic) plants or plant cells are produced by the known methods, for example by leaf-disc transformation (for example Horsch et al. 1985), by cocultivation of regenerating plant protoplasts or cell cultures with *Agrobacterium tumefaciens* (for example Marton et al. 1979, Hain et al. 1985) or by direct DNA transfection. Resulting transformed plants are detected either by selection for reporter gene expression, for example for in-vitro phosphorylation of kanamycin sulphate (Reis et al. 1984; Schreier et al. 1985), or by the expression of nopalin synthase (following the method of Aerts et al. 1983).

The resistance factors, for example the chitinase, can also be detected in the transformed plants in a known manner, with the aid of specific antibodies.

Culture of the transformed plant cells and regeneration to give complete plants are carried out by the generally customary methods with the aid of the nutrient media which are suitable in each case.

The transgenic plant cells as well as the transgenic plants, all of which contain resistance genes, or gene units, according to the invention and which are components of the present invention, show considerably increased resistance to pests, in particular phytopathogenic fungi.

The term "plants" in connection with the present invention denotes complete plants as well as parts of plants, such as leaves, seeds, tubers, cuttings etc. "Plant cells" include protoplasts, cell lines, plant calli etc. "Propagation material" denotes plants (as defined above) and plant cells (as defined above) which can be used for propagating the transgenic plants and plant cells. Propagation material of the transgenic plants according to the invention is also part of the present invention.

The present invention also includes genes and portions of genes as well as DNA sequences with "DNA sequences which act in essentially the same fashion". The genes, portions of genes and DNA sequences can exist in their genomic form and can also contain, for example, non-encoding portions such as introns. They can also exist in completely, or partially, chemically-synthesised form.

The term "DNA sequences which act in essentially the same fashion" in the present connection means that the invention also comprises those modifications in which the function of the resistance genes and portions thereof are not restricted in such a way that the resistance factors are no longer formed or that the regulatory gene portion is no longer effective. In the case of the cDNA according to the invention, "DNA sequences which act in essentially the same fashion" means modifications which do not considerably impair the use according to the invention of the cDNA as a probe for locating the genes according to the invention. Modifications in question can be effected by the replacement, the addition and/or the removal of DNA sections, of individual codons and/or of individual nucleic acids.

"Mutants" in connection with the microorganisms which can be used according to the invention means those modified microorganisms which still show the features which are essential for carrying out the invention, in particular containing the plasmids in question.

The present invention will be illustrated in greater detail with the aid of the following exemplary embodiments:

1. Isolation of resistance genes from *Arachis hypogaea*

Deoxyribonucleic acid DNA from the *Arachis hypogaea* suspension cell line (Rolfs et al. 1981) is isolated, and one aliquot in each case is cleaved with a restriction endonuclease, preferably the enzymes HindIII or MboI. The DNA is then separated according to its fragment size with the aid of sedimentation centrifugation or with the aid of gel electrophoresis (Sambrook, Fritsch and Maniatis, 1989, Molecular Cloning; A Laboratory Manual 2nd Ed., Cold Spring Harbor Laboratory Press U.S.A.). In the case of a centrifugation, the fragments are separated on a preformed gradient of 30–10% K acetate solution in 10 mM tris-HCl pH 7.5. To suppress diffusion of the fragments as far as possible, the centrifugation is carried out in a preparative ultracentrifuge at the highest possible speed. In each case, not more than 100 µg of cleaved DNA are separated in a volume of ≦100 µl on a gradient (gradient volume approx. 13 ml). The size of the fractions chosen after centrifugation is selected depending on the desired resolution (for example per 200 µl). The fractions which contain fragments of a size of up to approx. 10 kb (HindIII) or of 10–20 kb (MboI) are cloned into the lambda vectors (lambda ZAP II or lambda FIX II; Stratagen GmbH, Heidelberg).

Cloning of the HindIII fragments in lambda ZAP II may be illustrated as an example of the establishment of a partial gene library. The commercially available vector is digested with SpeI and the sticky ends which form:

```
A                    ACT
TGATC are converted into TGATC
``` by partial filling-in with C and T, and the same treatment applies to the HindIII ends of the fragments to be cloned, that is to say;

```
A                    AAG
TTCGA is converted into TTCGA
``` using A and G.

In this way, ends are formed which, in spite of their different origin, can be linked to each other in the customary fashion. Since it is preferably fragments of up to 10 kbp which can be cloned into the vector lambda ZAP II, large fragments are again discriminated here. In this manner, parts of a gene library of groundnut are in each case established which contain the resistance genes in the sense of the invention. Vectors which contain these resistance genes can be identified unequivocally with the aid of the cDNA probe which is cloned into pR 3-7, and further purified. The purified nucleic acid which contains the resistance genes is then transferred into tobacco or other plants with the aid of the direct DNA transformation under the concomitant action of polyethylene glycol (PEG) or a particle-bombardment apparatus as well as other transformation methods such as, for example, with the aid of agrobacteria.

Using the DNA sequence identified as SEQ ID NO: 1 as a probe, several genomic clones were isolated from *Arachis hypogaea*. The nucleotide sequence of one of the genomic clones is depicted in FIGS. 1a through 1c, collectively and SEQ ID NO: 3 and is identified as genomic clone λchit2a. This genomic clone has been transferred to tobacco plants according to the protocol set forth in Example 2b, infra, and can be shown to be expressed therein, i.e., it is a functional gene.

Genomic clone λchit2a was isolated as follows: A genomic library was custom prepared (Stratagene Cloning Systems, 11011 North Torrey, Pines Road, La Jolla, Calif., 92037 U.S.A.) and amplified using nuclear DNA isolated from *Arachis hypogaea* cv. NC 4 cloned into λ Dash phages (Stratagene). Approximately 700,000 phages from the amplified library were grown on plates using *E. coli* P2 SRB (Stratagene) as plating bacteria. After formation of plaques, DNA from phages was transferred to Hybond-N hybridization membranes (Amersham). The plaques were screened using $^{32}$P-labelled SEQ ID NO: 1 as the hybridization probe. Prehybridization and hybridization conditions were stringent and were as follows: 5×SSC, 5×Denhardt's, 0.5% SDS, 150 µg/ml sheared salmon sperm DNA, 65° C. Washes were with 2×SSC, 1% SDS, 65° C. for 30 minutes. Two multiple plaques were isolated and further purified. The restriction patterns of the isolated DNA were shown to be identical. Therefore, one clone was chosen for further analysis and that clone was identified as genomic clone λchit2a.

The further analysis of genomic clone λchit2a revealed the following: Positions 1–1169 constitute the promoter; position 1126 constitutes a transcription start site; positions 1170–1636 constitute exon I: coding part; positions 1637–2555 constitute intron I; positions 2556–2922 constitute exon II: coding part; and 2923-3'-end constitute an untranslated region. In addition, the motif "agccgcc" known to be present in several pathogenesis related genes is found between position −109 and −103 with the g→a exchange at position −105 ("agccacc"). Positions refer to the transcription initiation site 44 bases upstream to the ATG translation start codon.

2. Transformation of tobacco
a) Tobacco shoot culture and isolation of tobacco protoplasts:

*Nicotiana tabacum* (Petit Havana SR1) is propagated as a sterile shoot culture on hormone-free LS medium (Linsmaier and Skoog 1965). Approximately every 6–8 weeks, shoot sections are transferred to fresh LS medium. The shoot cultures are maintained in a growth cabinet at 24–26° C. at 12 hours of light (1,000–3,000 lux).

For the isolation of leaf protoplasts, about 2 g of leaves (about 3–5 cm in length) are cut into small pieces (0.5 cm×1 cm) using a new razor blade. The leaf material is incubated for 14–16 hours at room temperature in 20 ml of enzyme solution consisting of K3 medium (Nagy and Maliga 1976), 0.4 molar sucrose, pH 5.6, 2% Zellulase R10 (Serva), 0.5% Macerozym R10 (Serva). After this, the protoplasts are separated from cell debris by filtration over 0.30 mm and 0.1 mm steel screens. The filtrate is centrifuged for 10 minutes at 100×g. During this centrifugation, intact protoplasts float and collect at the top edge of the enzyme solution in the form of a band. The pellet consisting of cell debris and the enzyme solution are removed by suction using a glass capillary. The precleaned protoplasts are made up to 10 ml using fresh K3 medium (0.4M sucrose as an osmotic) and refloated. The wash medium is removed by suction, and the protoplasts are diluted to 1–2×10$^5$/ml for culturing or for subsequent infection with agrobacteria (coculture). The protoplast concentration is determined in a counting chamber.

b) Transformation of regenerating tobacco protoplasts by coculture with *Agrobacterium tumefaciens*:

In what follows, the method of Marton et al. 1979 is used, with slight modifications. The protoplasts are isolated as described and incubated in K3 medium (0.4 molar sucrose, 0.1 mg/l of NAA, 0.2 ml in K3 medium (0.4 molar sucrose, 0.1 mg/l of NAA, 0.2 mg of kinetin) at a density of 1–2×10$^5$/ml for 2 days in the dark and for one to two days under weak light (500 lux) at 26° C. As soon as the first protoplast divisions take place, 30 µl of an agrobacterium suspension in minimal A (Am) medium (density about 10$^9$ agrobacteria/ml) are added to 3 ml of regenerating protoplasts. Coculture is performed for 3–4 days at 20° C. in the dark. The tobacco cells are then decanted into 12 ml centrifuge tubes, diluted to 10 ml with sea-water (600 mOsm/kg), and pelleted for 10 minutes at 60×g. This washing process is repeated once or twice so as to remove most of the agrobacteria. The cell suspension is cultured at a density of 5×10$^4$/ml in K3 medium (0.3 molar sucrose) with 1 mg/l of NAA (naphthyl-1-acetic acid), 0.2 mg/l of kinetin and 500 mg/l of the cephalosporin-antibiotic cefotaxim. The cell suspension is diluted every week using fresh K3 medium, and the osmotic value of the medium is gradually reduced by 0.05 molar sucrose (about 60 mOsm/kg) per week. The selection with kanamycin (100 mg/l of kanamycin sulphate (Sigma), 660 mg/g of active km) is initiated 2–3 weeks after coculture in agarose bead-type culture (Shillito et al. 1983). Kanamycin-resistant colonies can be distinguished from the background of retarded colonies 3–4 weeks after the beginning of the selection.

c) Direct transformation of tobacco protoplasts with DNA. Calcium nitrate/PEG transformation:

In a Petri dish, about 10$^6$ protoplasts in 180 µl of K3 medium are carefully mixed with 20 µl of aqueous DNA solution which contains 0.5 µg/µl of the DNA which contains the resistance gene and 0.5 µg/µl of pLGV neo 2103 (Hain et al. 1985). 200 µl of fusion solution (0.1 molar calcium nitrate, 0.45M mannitol, 25% polyethylene glycol (PEG 6000), pH 9) are subsequently added carefully. After 15 minutes, 5 ml of wash solution (0.275M calcium nitrate, pH 6) are added and, after a further 5 minutes, the protoplasts are transferred to a centrifuge tube and pelleted at 60×g. The pellet is taken up in a small amount of K3 medium and cultured as described in the section below. Alternatively, the protoplasts can be transformed as described by Hain et al. 1985. The transformation can also be carried out without the addition of the 0.5 µg/µl of pLGV neo 2103. Since no reporter gene is employed in this case, the resulting calli can be tested for the presence of the resistance gene with the aid of a dot-blot hybridisation. A hybridisation probe which can be used is the above-mentioned cDNA from pR 3-7. Other detection methods such as antibody assay can, of course, also be employed.

d) Culture of the protoplasts incubated together with DNA, and selection of kanamycin-resistant calli:

For the culture described below and for the selection of kanamycin-resistant colonies, a modified "bead-type culture" technique (Shillito et al. 1983) is used. One week after the protoplasts have been treated with DNA (cf. c), 3 ml of the cell suspension are mixed with 3 ml of K3 medium (0.3M sucrose+hormones; 1.2% (Seaplaque) LMT agarose (low-melting agarose, Marine Colloids) in 5 cm Petri dishes. For this purpose, agarose is autoclaved dry, K3 medium is added, and the mixture is briefly boiled up in a microwave oven. After the agarose has solidified, the agarose disc.; ("beads") together with the embedded tobacco microcalli are transferred into 10 cm Petri dishes for further culture and selection, and batches of 10 ml of K3 medium (0.3M sucrose, 1 mg/l of NAA, 0.2 mg/l of kinetin) and 100 mg/l of kanamycin sulphate (Sigma) are added. The liquid medium is changed every week. During this process, the osmotic value of the medium is gradually lowered.

The exchange medium (K3+km) is reduced every week by 0.05 molar sucrose (about 60 mOsm).

Selection diagram for kanamycin-resistant tobacco colonies after DNA transformation:

| 0.4 M | 0.3 M | 0.25 M | 0.20 M | 0.15M | 0.10 M | Sucrose in the liquid medium |
|---|---|---|---|---|---|---|
| U | ES | | | K | | |
| 1 | 2 | 3 | 4 | 5 | 6 | weeks after DNA uptake |

(K3 medium, 1 mg of NAA, 0.2 mg of kinetin)
U = DNA uptake
E = embedding in agarose
S = selection with kanamycin (100 mg/l of kanamycin sulphate)
K = kanamycin-resistant colonies can be distinguished clearly from the background.

e) Regeneration of kanamycin-resistant plants:

As soon as the kanamycin-resistant colonies have reached a diameter of about 0.5 cm, half of them are placed on regeneration medium (LS medium, 2% of sucrose, 0.5 mg/l of benzylaminopurine BAP), and the cultures are maintained in a growth cabinet at 24° C. with 12 hours of light (3,000–5,000 lux). The other half is propagated as a callus culture on LS medium containing 1 mg/l of NAA, 0.2 mg/l of kinetin, 0.1 mg/l of BAP and 100 mg/l of kanamycin sulphate. When the regenerated shoots have a size of about 1 cm, they are excised and placed on ½ LS medium (1% sucrose, 0.8% agar) without growth regulators, for rooting. The shoots are rooted on ½ MS medium containing 100 mg/l of kanamycin sulphate, and later transplanted into soil.

f) Transformation of leaf discs by *Agrobacterium tumefaciens*:

For the transformation of leaf discs (Horsch et al. 1985), leaves, about 2–3 cm in length, of sterile shoot cultures, are punched into discs of diameter 1 cm, and the discs are incubated for about 5 minutes with a suspension of appropriate agrobacteria (about $10^9$/ml) (cf. b) in Am medium, see below). The infected leaf portions are maintained on MS medium (see below) without hormones for 3–4 days at about 24° C. During this time, agrobacterium covers the leaf portions with growth. The leaf portions are subsequently washed in MS medium (0.5 mg/ml of BAP, 0.1 mg/ml of NAA) and placed on the same medium (0.8% agar) containing 500 µg/µl of cefotaxim and 100 µg/µl of kanamycin sulphate (Sigma). The medium should be renewed after two weeks. Transformed shoots become visible after a further 2–3 weeks. The regeneration of shoots should also be carried out in parallel without selection pressure. The regenerated shoots must then be tested for transformation, using biological tests, for example for nopalin synthase or resistance gene activity. 1–10% of transformed shoots are obtained in this manner.

g) Biochemical method for detecting transformation Detection of nopalin in plant tissues:

Nopalin is detected as follows, as described by Otten and Schilperoort (1978) and Aerts et al. (1979). In an Eppendorf container, 50 mg of plant material (callus or leaf portions) are incubated overnight in LS medium containing 0.1M arginine at room temperature. The plant material is then dabbed with absorbent paper, homogenised in a new Eppendorf centrifuge container using a glass rod, and the homogenate is centrifuged for 2 minutes in an Eppendorf centrifuge. 2 µl of the supernatant are applied to a sheet of paper (20×40 cm) which is suitable for electrophoresis (Whatman 3 MM paper) in the form of small spots and dried. The sheet of paper is saturated with the mobile phase (5% formic acid, 15% acetic acid, 80% $H_2O$, pH 1.8), and electrophoresis is carried out for 45 minutes at 400 V. Nopalin migrates to the cathode. The sheet of paper is then dried in a stream of hot air and pulled through phenanthrenequinone stain (equal volumes of 0.02% phenanthrenequinone in ethanol and 10% NaOH in 60% ethanol) in the direction of movement. The dried sheet of paper is viewed under long-wave UV light, and photographs are taken. The reagent stains arginine and arginine derivatives fluorescent yellow.

Neomycin phosphotransferase (NPT II) enzyme assay:

NPT II activity in plant tissues is detected by in-situ phosphorylation of kanamycin, as described by Reiβ et al. (1984) and modified by Schreier et al. (1985), as follows. 50 mg of plant tissue are homogenised in 50 µl of extraction buffer (10% glycerol, 5% 2-mercaptoethanol, 0.1% SDS, 0.025% Bromophenol Blue, 62.5 mM tris pH 6.8) with the addition of glass powder, on ice, and the homogenate is centrifuged for 10 minutes in an Eppendorf centrifuge at 4° C. 50 µl of the supernatant are applied to a native polyacrylamide gel (145×110×1.2 mm; separating gel: 10% acrylamide, 0.33% bisacrylamide, 0.375M tris pH 8.8, collecting gel: 5% acrylamide, 0.165% bisacrylamide, 0.125M tris pH 6.8) and the gel is subjected to electrophoresis overnight at 4° C. and 60 V. As soon as the Bromophenol Blue marker migrates out of the gel, the gel is washed twice with distilled water for 10 minutes and once with reaction buffer (67 mM tris maleate, pH 7.1, 42 mM $MgCl_2$, 400 mM ammonium chloride) for 30 minutes. The gel is placed on a glass plate of equal size and covered with 40 ml of 1% strength agarose in reaction buffer containing the substrates kanamycin sulphate (20 µg/ml) and 20–200 µCi $^{32}$p ATP (Amersham). The sandwich gel is incubated for 30 minutes at room temperature, and a sheet of phosphocellulose paper P81 (Whatman) is then placed on the agarose. Four layers of filter paper 3 MM (Whatman) and some paper towels are then placed on top of this. The transfer of in-situ phosphorylated radioactive kanamycin phosphate to the P81 paper is stopped after 3–4 hours. The P81 paper is incubated for 30 minutes in a solution of proteinase K and 1% sodium dodecyl sulphate (SDS) at 60° C. and then washed 3–4 times in 250 ml of 10 mM phosphate buffer pH 7.5 at 80° C., dried, and autoradiographed for 1–12 hours at −70° C. (XAR5 film Kodak).

3. Transformation of Medicago sativa (Lucerne)

a) Plant material

The plant *Medicago sativa* (Regen S, clone RA3 Walker et al., 1978) is cultured as a sterile shoot culture on LS medium (Linsmaier and Skoog, 1965), under long-day conditions (16 h light, 8 h dark) at 26±2° C.

b) Culture conditions

Glass containers (250 ml–1.5 l), covered loosely with glass lids, are used as culture containers for shoot cultures. Plastic Petri dishes are used for all other plant cultures (embryo, callus, protoplasts).

Except for the protoplasts, the plants and tissue cultures are cultured in growth cabinets under long-day conditions (16 h light, 8 h dark) at 26±2° C. The fluorescent tubes have the light colour Universal White (Osram L58W/25). The tubes are arranged at a distance from the cultures of 10–30 cm, which corresponds to a light intensity of 1,500–4,500 lux. The atmospheric humidity remains unregulated. The protoplasts are cultured in incubators at not more than 500 lux and 26° C.

a) Callus culture

Callus is induced by petioles of the greenhouse plants. Petiole segments approx. 5 cm in length are excised from the greenhouse plants using a surgical blade. First, the petiole segments are surface-sterilised:

1 minute in 70% ethanol 10 minutes in 10% strength commercially available disinfectant (for example Dan Klorix)

3 washes in sterile tap water.

After sterilisation, the petiole segments are cut into segments 1–1.5 cm in length, and these are placed on solid agar medium in Petri dishes. Three different media are used for callus induction and further culture:

1. $B_5h$ (Atanassov and Brown, 1984)
2. SHR: SH (Shenk and Hildebrandt, 1972) with 25 µM (4.655 mg/l) NAA and 10 µM (2.15 mg/l) kinetin (Walker and Sato, 1981)
3. $B_5H_3$: $B_5$ (Gamborg et al., 1968) with 2.6 µM (0.5 mg/l) NAA, 2.2 µM (0.5 mg/l) BAP, 2.2 µM (0.5 mg/l) 2.4 D (Oelck, dissertation 1984).

After three weeks, the outer portions of each callus are excised using a surgical blade and subcultured on fresh medium.

d) Callus regeneration

Plants are regenerated from Callus following the protocol of Stuart and Strickland, 1984 a, b, with modifications.

Somatic embryogenesis is induced by incubation of callus tissue in liquid SH medium (Shenk and Hildebrandt, 1972) which contains 50 µM (11 mg/l) 2,4 D and 5 µM (1.07 mg/l) kinetin. In an Erlenmeyer flask (100 ml in a 500 ml flask), 30 mg of callus (fresh weight) are added per ml of medium. Induction is effected for 3–4 days on a shaker (100 rpm) at 26° C. in a plant growth cabinet. The callus tissue is subsequently separated from the medium on a screen (850 µm²).

It is pressed through the screen using a spatula, and small cell aggregations are collected on a screen of mesh size 250 $\mu m^2$ which is located under the first screen. Per 100 ml of induction medium, the cell aggregations are washed with 500 ml of SHJ medium without hormones (SH). As much as possible of the wash solution is removed by allowing it to run off (approx. 5 minutes). The fresh weight is determined, and the cell aggregations are resuspended in SH medium. In a pipette, 75 mg in 0.5 ml are applied to approx. 10 ml of solid regeneration medium SHR. The regeneration medium SHR consists of SH medium with 25 mM $NH_4^+$ and 100 mM L-proline in 3% sucrose.

After approx. four weeks, well developed embryos with a noticeable polarity (cotyledon stage, Dos Santos et al., 1983) are placed on solid ½ SH medium with 25 $\mu M$ (8.6 mg/l) gibberellic acid ($GA_3$) and 0.5 $\mu M$ (0.046 mg) NAA. After the development of roots and a shoot with leaves, the small plantlets are transferred to LS medium.

The table shows the composition of the media $B_5h$, SHJ, SHR, ½ SH and LS. The liquid medium SH corresponds to the SHJ medium without the hormones 2,4 D and kinetin. Unless otherwise stated, amounts are given in mg/l.

|  | $B_5h$ | SHJ | SHR | ½ SH | LS |
|---|---|---|---|---|---|
| Macroelements |  |  |  |  |  |
| $NH_4NO_3$ | — | — | — | — | 1650 |
| $KNO_3$ | 3000 | 2500 | 2500 | 1250 | 1900 |
| $CaCl_2\ 2H_2O$ | 895 | 200 | 200 | 100 | 1900 |
| $MgSO_4\ 7H_2O$ | 500 | 400 | 400 | 200 | 370 |
| $(NH_4)_2SO_4$ | 134 | — | 1651 | — | — |
| $NaH_2PO_4H_2O$ | 156 | — | 407 | — | — |
| $KH_2PO_4H_2O$ | — | — | — | — | 170 |
| $NH_4H_2PO_4$ | — | 300 | — | 150 | — |
| Microelements |  |  |  |  |  |
| $ZnSO_4H_2O$ | 10 | 10 | 10 | 5 | 22.3 |
| $H_3BO_3$ | 3 | 5 | 5 | 2.5 | 6.2 |
| $ZnSO_4\ 7H_2O$ | 1 | 1 | 1 | 0.5 | 8.6 |
| $Na_2MoO_4 2H_2O$ | 0.25 | 0.1 | 0.1 | 0.05 | 0.25 |
| $CuSO_4\ 5H_2O$ | 0.025 | 0.02 | 0.02 | 0.1 | 0.025 |
| $CaCl_2\ 6H_2O$ | 0.025 | 0.1 | 0.1 | 0.05 | 0.025 |
| KJ | 0.75 | 1 | 1 | 0.5 | 0.83 |
| $FeSO_4\ 7H_2O$ | 28 | 15 | 15 | 7.5 | 28 |
| $Na_2EDTA$ | 37 | 20 | 20 | 10 | 37 |
| Vitamins |  |  |  |  |  |
| Thiamine HCl | 10 | 5 | 5 | 2.5 | 0.4 |
| Pyridoxine HCl | 1 | 0.5 | 0.5 | 0.25 | — |
| Nicotinic acid | 1 | 5 | 5 | 2.5 | — |
| Amino acids |  |  |  |  |  |
| L-Glutamine | 800 | — | — | — | — |
| L-Serine | 100 | — | — | — | — |
| L-Proline | — | — | 5755 | — | — |
| Other components |  |  |  |  |  |
| Inter alia, phytohormones |  |  |  |  |  |
| Myo-inositol | 100 | 1000 | 1000 | 500 | 100 |
| L-glutathione | 10 | — | — | — | — |
| Adenine sulphate | 1 | — | — | — | — |
| 2,4-D | 1 | 11.5 | — | — | — |
| Kinetin | 0,2 | 1,075 | — | — | — |
| $GA_3$ | — | — | — | 8.6 | — |
| NAA | — | — | — | 0.046 | — |
| Sucrose | 30 g | 30 g | 30 g | 15 g | 10 g |
| pH | 5.8 | 5.9 | 5.9 | 5.9 | 5.8 |

The pH is adjusted using 1N KOH.

The media are sterilised by heating in the autoclave for 17 minutes at 121° C. Kinetin, L-glutathione and amino acids are filter-sterilised and added to the medium after heating in the autoclave, the temperature of the medium being 60° C.

e) Protoplast culture

The starting material used for isolating protoplasts are the leaves of 2–3 month old sterile shoot cultures. They are harvested 2–3 hours after switching on the light.

In a Petri dish, the leaves are first moistened with EMI (Atanassov and Brown, 1984) and cut up finely using a new razor blade.

In a Petri dish ($\phi$10 cm), 1–1.5 g of leaves are then incubated for 3–4 hours together with 10 ml of enzyme solution. Incubation is carried out at 26° C. and weak illumination. The emergence of protoplasts from the leaves is monitored under a microscope. Every 30 minutes, the dish is shaken gently 2–3 times.

The enzyme solution consists of a 1:1 mixture of Atanassov and Brown's (1984) protoplast culture medium (AP) with the hormones 0.2 mg/l of 2,4-D, 0.5 mg/l of zeatin and 1 mg/l of NAA and an enzyme solution. The enzyme solution (Kao and Michayluk, 1979; modified) consists of:

| | |
|---|---|
| 200 mg of Cellulose Onozuka R10 | Serva |
| 80 mg of Macerozyme R10 | Sigma |
| 10 mg of Pectolyase Y-23 | |
| 540 mg of sorbitol | | f) Transformation of an induced callus

Callus is induced to embryogenesis by the method which is described under callus regeneration.

Following the incubation for 3–4 days in liquid SHJ, the callus material is washed on a screen (mesh size 100 $\mu m$) with liquid SHR which contains no agar and no L-proline. The callus material is then taken up in liquid SHR. To approx. 1 g of callus material, 10 ml of medium are added.

After the agrobacteria which contain Ti plasmids carrying resistance gene have been added ($2\times10^7$/ml end concentration), the callus material is incubated for 2–3 days at 26° C., on a shaker (90 rpm).

On a screen (mesh size 100 $\mu m^2$), the material is then washed with liquid SHR.

Plating (75 mg of callus/10 ml of medium) is effected on the normal solid SHR with 100 mM L-proline. Besides the selective antibiotics, the medium in the plates contains 500 $\mu$g/ml of claforan. After four weeks, the resistant structures are placed on fresh antibiotics-containing medium, and, after a further three weeks, they are divided, and one half is placed on fresh medium without selective antibiotics and the other half is placed on antibiotics-containing medium.

g) Transformation of embryos

The transformation of embryos is carried out analogously to the transformation Of the induced callus. The starting material used are 4–5 week old embryos. In a Petri dish, they are cut up finely using a razor blade and then washed on a screen (mesh size 100 $\mu m$) using liquid SHR. Approx. 1 g of cut-up embryos are taken up in 10 ml of liquid SHR. After the agrobacteria have been added ($2\times10^7$/ml end concentration), they are incubated for 2–3 days at 26° C. on a shaker (90 rpm). After this, the embryo portions are washed on a screen (100 $\mu m^2$) using liquid SHR. Using a spatula, they are plated on plates which contain the standard solid SHR with 100 mM L-proline. Per plate containing 10 ml of medium, approx. 50–100 mg of embryo portions are distributed. Besides the selective antibiotics, the medium in the plates contains 500 $\mu$g/ml of claforan. Three weeks after plating, the secondary embryos are subcultured-on fresh plates. Well developed embryos are transplanted to antibiotics-free ½ SH medium (Stuart and Strickland, 1984, b) to allow further development into plants. Small rooted plantlets are then transplanted to LS medium.

4. Transformation of *Solanum tuberosum* (potato)

The transformation was transformed precisely in the manner given in EP-A-0,242,246, pages 14 to 15, the agrobacteria containing Ti plasmids carrying the resistance gene.

All percentages in the above examples relate to per cent by weight, unless indicated otherwise.

In the transgenic plant cells and plants obtained in accordance with the above examples, the transfer and the expression of the resistance genes can be detected clearly by the generally customary methods with the aid of two criteria. For example, the genes and their primary gene products can be detected clearly with the aid of the abovementioned test. Furthermore, the primary gene products are preferentially expressed when the transgenic plants were infected with a pathogen, for example by *Phytophthora megasperma* or its cell wall fragments. The biological action in the sense of an increased resistance to harmful organisms can be detected by reduced growth of the pathogens and by a reduced damage to plants.

In what follows, some of the media employed in the transformation of plants, or plant cells, are described;

Am medium 3.5 g of $K_2HPO_4$
1.5 g of $KH_2PO_4$
0.5 g of $Na_3$ citrate
0.1 g of $MgSO_4 \times 7H_2O$
1 g of $(NH_4)_2SO_4$
2 g of glucose
to 1 l Medium for sterile shoot culture of tobacco

| Macroelements ½ of the concentration of the MS salts | | |
|---|---|---|
| Microelements ½ of the concentration of the MS salts | | |
| Murashige and Skoog (MS) | | |
| Fe EDTA | | |
| Myo-inositol | 100 | mg/l |
| Sucrose | 10 | mg/l |
| Agar | 8 | mg/l |
| Vitamins | | |
| Ca pantothenate | 1 | mg/l |
| Biotin | 10 | mg/l |
| Nicotinic acid | 1 | mg/l |
| Pyridoxine | 1 | mg/l |
| Thiamine | 1 | mg/l | pH 5.7 before autoclaving

K3 medium

For culturing *Nicotiana tabacum* petit Havana SR1, *Nicotiana tabacum* Wisconsin 38, and *Nicotiana plumbaginifolia* protoplasts (Nagy and Maliga, 1976)

| Macroelements | | |
|---|---|---|
| $NH_4NO_3$ | 250 | mg/l |
| $KNO_3$ | 2,500 | mg/l |
| $CaCl_2 \times 2H_2O$ | 900 | mg/l |
| $MgSO_4 \times 7H_2O$ | 250 | mg/l |
| $NaH_2PO_4 \times 1H_2O$ | 150 | mg/l |
| $(NH_4)_2SO_4$ | 134 | mg/l |
| $CaHPO_4 \times 1H_2O$ | 50 | mg/l |
| Microelements | | |
| $H_3BO_3$ | 3 | mg/l |
| $MnSO_4 \times 1H_2O$ | 10 | mg/l |
| $ZnSO_4 \times 4H_2O$ | 2 | mg/l |
| KI | 0.75 | mg/l |
| $Na_2MoO_4 \times 2H_2O$ | 0.25 | mg/l |
| $CuSO_4 \times 5H_2O$ | 0.025 | mg/l |
| $CoCl_2 \times 6H_2O$ | 0.025 | mg/l |
| Fe EDTA | | |
| $Na_2EDTA$ | 37.2 | mg/l |
| $FeSO_4 \times 7H_2O$ | 27.8 | mg/l |
| Inositol | 100 | mg/l |
| Sucrose | 137 | g/l (= 0.4 M) |
| Xylose | 250 | mg/l |
| Vitamins | | |
| Nicotinic acid | 1 | mg/l |
| Pyroxine | 1 | mg/l |
| Thiamine | 10 | mg/l |
| Hormones | | |
| NAA | 1.0 | mg/l |
| Kinetin | 0.2 | mg/l | pH 5.6
Filter-sterilisation

Linsemaier and Skoog medium (Linsmaier and Skoog 1965)

For culturing regenerating protoplasts and for tissue culture of tobacco tumours and callus. Linsmaier and Skoog (LS) medium is Murashige and Skoog medium (Murashige and Skoog, 1962) with the following modifications:

The thiamine weighed in is more concentrated 0.4 mg/l instead of 0.1 mg/l;

No glycine, pyridoxine and nicotinic acid.

| Macroelements | | |
|---|---|---|
| $NH_4NO_3$ | 1,650 | mg/l |
| $KNO_3$ | 1,900 | mg/l |
| $CaCl_2 \times 2H_2O$ | 440 | mg/l |
| $MgSO_4 \times 7H_2O$ | 370 | mg/l |
| $KH_2PO_4$ | 170 | mg/l |
| Microelements | | |
| $H_3BO_3$ | 6.2 | mg/l |
| $MnSO_4 \times 1H_2O$ | 22.3 | mg/l |
| $ZnSO_4 \times 4H_2O$ | 8.6 | mg/l |
| KI | 0.83 | mg/l |
| $Na_2MoO_4 \times 2H_2O$ | 0.25 | mg/l |
| $CuSO_4 \times 5H_2O$ | 0.025 | mg/l |
| $CoCl_2 \times 6H_2O$ | 0.025 | mg/l |
| Fe EDTA | | |
| $Na_2EDTA$ | 37.2 | mg/l |
| $FeSO_4 \times 7H_2O$ | 27.8 | mg/l |
| Inositol | 100 | mg/l |
| Sucrose | 30 | g/l |
| Agar | 8 | g/l |
| Vitamins | | |
| Thiamine | 0.4 | mg/l |
| Hormones | | |
| NAA | 1 | mg/l |
| kinetin | 0.2 | mg/l | pH 5.7 before autoclaving.

The following literature on the transformation of plants or plant cells and on the subject of resistance genes can be mentioned to further illustrate the methods and techniques employed:

Aerts M., Jacobs M., Hernalsteens J. P., Van Montagu M., Schell J. (1983) Induction and in vitro culture of *Arabidopsis thaliana* crown gall tumours. Plant Sci Lett. 17: 43–50

Atanasov A., Brown D. C. W. (1984) Plant regeneration from suspension culture and mesophyll protoplasts of *Medicago sativa* L. Plant Cell Tiss Org. Cult. 3, 149–162

Davey M. R., Cocking E. C., Freeman J., Pearce N., Tudor I. (1980) Transformation of Petunia protoplasts by isolated Agrobacterium plasmid. Plant Sci Lett 18: 307–313

Deblaere R., Bytebier B., De Greve H., Deboeck F., Schell J., van Montagu M., Leemans J. (1985) Efficient octopine Ti plasmid-derived vectors for Agrobacterium-mediated gene transfer to plants. Nucleic Acid Research, Vol. 13, No. 13, 4777 (1985)

Fraley R. T. et al., Proc. National Acad. Sci U.S.A. 80, 4803 (1983)

Fromm M. E., Taylor L. P., Walbot V. (1986) Stable transformation of maize after gene transfer by electroporation. Nature 319: 791–793

Gamborg O. L., Miller R. A. and Ojiima K. (1968) Nutrient requirements of suspension cultures of soybean root cells, Experimental Cell Research 50: 151–158

Hain, R., Stabel, P., Czernilofsky, A. Pp., Steinbiβ, H. H., Herrera-Estrella, L., Schell, J. (1985) Uptake, integration, expression and genetic transmission of a selectable chimeric gene by plant protoplasts. Molec Gen Genet 199: 161–168

Herrera-Estrella L., De Block M., Lessens E., Hernalsteens J. P., van Montagu M., Schell J. (1983) EMBO J. 2: 987–995.

Horsch R. B., Fry J. E., Hoffmann N. L., Eichholtz D., Rogers S. G., Fraley R. T. (1985) A simple and general method for transferring-genes into plants. Science 277: 1229–1231

Kao K. N., Michayluk M. R. (1980) Plant regeneration from Mesophyll protoplasts of Alfalfa. Z Pflanzenphysiol. 96, 135–141

Keller W. A., Melchers G. (1973) The effect of high pH and calcium on tobacco leaf protoplast fusion. Z Naturforschg 28c: 737–741

Krens F. H., Molendijk L., Wullems G. J., Schilperoort R. A. (1982) in vitro transformation of plant protoplasts with Ti-plasmid DNA. Nature 296: 72–74 Koncz C., Schell J. (1986) The promotor of $T_L$-DNA gene 5 controls the tissue-specific expression of chimaeric genes carried by a novel type of Agrobacterium linary vector. Mol. Gen. Genet. (1986) 204: 338–396

Linsmaier D. M., Skoog F. (1965) Organic growth factor requirements of tobacco tissue cultures. Physiol Plant 18: 100–127

Marton L., Wullems G. J., Molendijk L., Schilperoort P. R. (1979) In vitro transformation of cultured cells from *Nicotiana tabacum* by *Agrobacterium tumefaciens*. Nature 277: 1229–131

Nagy J. I., Maliga P. (1976) Callus induction and plant regeneration from mesophyll protoplasts of *Nicotiana sylvestris*, Z Pflanzenphysiol 78: 453–455

Oelck Michael M., Dissertation, 1984, University of Cologne, Federal Republic of Germany, Regeneration von Leguminosen aus Gewebe—und Zellkulturen [Regeneration of legumes from tissue and cell cultures]

Otten L. A. B .M., Schilperoort R. A. (1973) A rapid microscale method for the detection of Lysopin and Nopalin dehydrogenase activities. Biochim biophys acta 527: 497–500

Paszkowski J., Shillito R. D., Saul M, Mandak V., Hohn T., Hohn B., Potrykus I. (1984) Direct gene transfer to plants. EMBO J 3: 2717–2722

Rolfs, Fritzemeier, Kindl (1981) Plant Cell Reports 1: 83–85

Reiss Bernd, Sprengel Rolf, Will Hans and Schaller Heinz (1984) A new sensitive method for qualitative and quantitative assay of neomycin phosphotransferase in crude cell tracts, GENE 1081: 211–17

Sambrook, Fritsch und Maniatis, 1989, Molecular Cloning; A Laboratory Manual 2nd Ed., Cold Spring Harbor Laboratory Press U.S.A.

Schreier Peter H., Seftor Elisabeth A., Schell Jozef and Bohnert Hans J. (1985) The use of nuclear-encoded sequences to direct the light-regulated synthesis and transport of a foreign protein into plant chloroplasts, EMBO J Vol. 4, No. 1: 25–32

Shenk R. U., Hildebrandt A. C. (1972) Medium and techniques for induction and growth of monocotyledonous and dicotyledonous cell cultures. Ca. J. Bot. 50, 199–204

Shillito R. D., Paszkowski J. Potrykus I. (1983) Agarose plating and Bead type culture technique enable and stimulate development of protoplast-derived colonies in an number of plant species. Pl Cell Rep 2: 244–247

Simons-Schreier A., Dissertation at Cologne University (1988) Studien zur Transformation von *Medicago sativa* und zur Expression eines Leghämoglobingens (1bc3) und eines chimären 1b-cat-Gens während der Symbiose in transgenen Pflanzen [Studies into the transformation of *Medicago sativa* and into the expression of a leghaemoglobin gene (1bc3) and a chimeral 1b-cat gene during symbiosis in transgenic plants]

Stuart D. A., Strickland S. G. (1984) Somatic embryogenesis from cell cultures of *Medicago sativa* L. I. The role of amino acid additions to the regeneration medium. Plant Sci. Let. 34, 165–174

Stuart D. A., Strickland S. G. (1984) Somatic embryogenesis from cell cultures of *Medicago sativa* L. II. The interaction of amino acids with ammonium. Plant Sci. Let. 34, 175–181

Van den Elzen P. J. M., Townsend J. Lee K. Y., Bedbrook J. R. (1985) Achimaeric resistance gen as a selectable marker in plant cells. Plant Mol. Biol. 5, 299–332.

Velten J. Velten L., Hain R., Schell J. (1984) Isolation of a dual plant promoter fragment from the Ti Plasmid of *Agrobacterium tumefaciens*. EMBO J 12: 2723–2730

Walker K. A., Yu P. C., Sato S. J., Jaworski E. G. (1978) The hormonal control of organ formation in callus of *Medicago sativa* L. cultured in vitro. Amer. J. Bot. 65(6), 654–659

Walker K. A., Sato S. J. (1981) Morphogenesis in callus tissue of *Medicago sativa*. The role of ammonium ion in somatic ambryogenesis. Plant Cell Tiss. Org. Cult. 1, 109–121

Wullems G. J., Molendijk L., Ooms G., Schilperoort R. A. (1981) Differential expression of crown gall tumor markers in transformants obtained after in vitro *Agrobacterium tumefaciens*—induced transformation of cell wall regenerating protoplasts derived from *Nicotiana tabacum*. Proc Natl Acad Sci 78: 4344–4348

Yanisch-Perron, C., Vicira, J. und Messing, J. (1985) Gene 33, 103–119

Zambryski P., Joos H., Genetello C., van Montagu M., Schell J. (1983) Ti-plasmid vector for the introduction of DNA into plant cells without altering their normal regeneration capacity, EMBO J 12: 2143–2150.

The following published patent applications can furthermore be mentioned:

EP-A 116,718
EP-A 159,418
EP-A 120,515

EP-A-120,516
EP-A-172,112
EP-A-140,556
EP-A-174,166
EP-A-122,791
EP-A-126,546
EP-A-164,597
EP-A-175,966

EP-A-270,822
WO 84/02913
WO 84/02919
WO 84/02920
WO 83/01176

It will be understood that the specification and examples are illustrative but not limitative of the present invention and that other embodiments within the spirit and scope of the invention will suggest themselves to those skilled in the art.

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 170 nucleotides
      (B) TYPE: Nucleic acid
      (C) STRANDEDNESS: Double
      (D) TOPOLOGY: Linear (ii) MOLECULE TYPE: cDNA from mRNA (v) FRAGMENT TYPE: Part of cDNA from mRNA (vi) ORIGINAL SOURCE:
      (A) ORGANISM: Peanut (arachis hypogaea)
      (H) CELL LINE: Cell Culture (ix) FEATURE:
      (C) IDENTIFICATION METHOD: Oligonucleotides and PCR (x) PUBLICATION INFORMATION:
      (A) AUTHORS: Thomas Herget; Jeff Schell; and Peter H. Schreier
      (B) TITLE: Elicitor-Specific Induction of One Member of the Chitinase Gene Family in Arachis Hypogaea
      (C) JOURNAL: Mol. Gen. Gent.
      (D) VOLUME: 224
      (E) ISSUE:
      (F) PAGES: 469-476
      (G) DATE: 1990
      (H) DOCUMENT NUMBER:
      (I) FILING DATE:
      (J) PUBLICATION DATE:
      (K) RELEVANT RESIDUES IN SEQ ID NO:

(xi) SEQUENCE DESCRIPTION: SEQ ID NO:1:

```
ATC TCG TTC AAG TCG GCG CTC TGG TTG TGG ATG ACA GAG                    39
Ile Ser Phe Lys Ser Ala Leu Trp Leu Trp Met Thr Glu
1               5                       10

CAG AAA CCA AAA CCT TCT TGC CAC AAC GTC ATG GTT GGG                    78
Gln Lys Pro Lys Pro Ser Cys His Asn Val Met Val Gly
        15                  20                  25

AAT TAC GTG CCA ACA GCA TCT GAT AGA GCA GCA AAT AGA                   117
Asn Tyr Val Pro Thr Ala Ser Asp Arg Ala Ala Asn Arg
                30                  35

ACC TTA GGG TTT GGG TTG GTT ACG AAC ATC ATC AAC GGC                   156
Thr Leu Gly Phe Gly Leu Val Thr Asn Ile Ile Asn Gly
40                  45                  50

GGC CTG GAC TGC GG                                                    170
Gly Leu Asp Cys
        55
```

(2) INFORMATION FOR SEQ ID NO: 2:

(i) SEQUENCE CHARACTERISTICS:
        (A) LENGTH: 227 nucleotides
        (B) TYPE: Nucleic acid
        (C) STRANDEDNESS: Double
        (D) TOPOLOGY: Linear (ii) MOLECULE TYPE: cDNA from mRNA (fragment)

(vi) ORIGINAL SOURCE:
        (A) ORGANISM: Peanut (arachis hypogaea)

(xi) SEQUENCE DESCRIPTION: SEQ ID NO:2:

```
GAATTCGAGC TCGGTACCCG GGGATCCTCT AGAGTC                              36

ATC TCG TTC AAG TCG GCG CTC TGG TTG TGG ATG ACA GAG                  75
Ile Ser Phe Lys Ser Ala Leu Trp Leu Trp Met Thr Glu
 1               5                  10

CAG AAA CCA AAA CCT TCT TGC CAC AAC GTC ATG GTT GGG                 114
Gln Lys Pro Lys Pro Ser Cys His Asn Val Met Val Gly
        15                  20                  25

AAT TAC GTG CCA ACA GCA TCT GAT AGA GCA GCA AAT AGA                 153
Asn Tyr Val Pro Thr Ala Ser Asp Arg Ala Ala Asn Arg
                30                  35

ACC TTA GGG TTT GGG TTG GTT ACG AAC ATC ATC AAC GGC                 192
Thr Leu Gly Phe Gly Leu Val Thr Asn Ile Ile Asn Gly
40                  45                  50

GGC CTG GAC TGC GGGACCTGCA GGCATGCAAG CTT                           227
Gly Leu Asp Cys
        55
```

(2) INFORMATION FOR SEQ ID NO: 3:

(i) SEQUENCE CHARACTERISTICS:
        (A) LENGTH: 3412 nucleotides
        (B) TYPE: Nucleic acid
        (C) STRANDEDNESS: Double
        (D) TOPOLOGY: Linear (ii) MOLECULE TYPE: Genomic DNA (vi) ORIGINAL SOURCE:
        (A) ORGANISM: Peanut (arachis hypogaea)

(xi) SEQUENCE DESCRIPTION: SEQ ID NO:3:

```
ATCGATACCA TGTGTCCATA TTTTTATACT TTTAGCCTCA AATTCTTTCA              50

TTTCTTAAGA GTATAAAGAC ATAATATTAT CTATCAACCT ATTATATTAT             100

TATTAGGGTG GCATGTATGC ATAGGTTCTA TGGCTAGTCT CGTATTTATT             150

CAAAGGTGAA TTTTAACAAA ACTATGAATG GTATAGTTTT TAAATGGGTT             200

TATAAGTGTT AGTCATTCCT CGCTTTTTGA ATTAGTTTTT TGAATTGAGG             250

TAGACTCGTT CAAACTCAAT TTTAATATAA GAAAAAAAAT ATTAAGGATG             300

TTACAAATAA AAATTTTAAT AAACAATATT ACTTTTTAAA AATTTTCAAT             350

ACAATAAAAT GTATGGAAAA ATGCTAAAAC TTTTTATTTT ACCTTCGTTA             400

ACTAATGCCG AAAGTCCAAT CCCATTTTCC TCCATTCATG GACTATGTCA             450

ATGTGACATG ATAATGATGG TTATCAAGAA CTCAAATTTT AGTACAACTG             500

GTATAAAAAA ATATTGAAAG TAATAGATAG ATTTGAGAAG TGAAATCAAA             550

TTATACATGA ATTGAAGAAT GACTCTGAAA CATCTTATTA ATCTCTTCCA             600

CCTCCACAAT GATATCACAC ACTCCAATTC ATAAATAAAA ACATAATTTT             650
```

```
TTATGCATCT TTTAATAATT TCAAAGTCTT ATGTTTAAGA TAGGAGGGCA        700

AAGATAACAA CAATATATGA TGGAAGCTTC AGAAAGTCAA AACTAGTTTA        750

GTCATCATTT TATATAAACT TGGAATGGTC CTCTCAATTA AATATGAGAG        800

AAGGATTCAA AGCCGAAAAC ATTTCTTTAA TTTTCATTCA AGTTCTCTAT        850

TATGTTACAA ATTTAGTATC AACAAATTAA TAACAAAGAA ATACATTATG        900

AAGCAGCTTG CCAAGTAGGA ACACACTAAA TGGGTTTCAT AATAAATGAT        950

GAACATATAA TGCGTTAGTG AGTAGGACAA CATAAACCGT TGACCTTTGA       1000

CCCTCCACGC CCACTAAGCC ACCACCGTCT TTTACCTTTG AATATACGAA       1050

ATCTTTGTGT AGCGTTGAGT ATTGATTATT GAAATTGTAC ATATATAAAC       1100

CTTAATCCTA CCTCATATCA TTCCCACATA AAACCAAAC CAATCCTTGA        1150

TAACATAACA TCCAATAACA TGGCATTATT CTCATTCTCA TTCTCCTCAT       1200

TCTGCCTCAC AATTTTTGTC ATCTATTCTT CTTTATCTCT ATCTGCTGAA       1250

TCACGTGTCT CACCAATTGC ACCAATCTCT TCTCTCATTA GCAAAACCCT       1300

TTTCGACTCA ATCTTTTTAC ATAAAGATGA CAATGCTTGC CCTGCTAGAA       1350

ACTTTTACAC TTATGAATCC TTCGTTGAGG CAACCTCGAG CTTCCCAGCG       1400

TTCGGCTCGA CCGGATGCTC GGCCACACGG AAGCGCGAGG TTGCCGCATT       1450

TCTTGCACAG ATCTCACATG AAACCACAGG TGGTTGGGCT ACTGCACCTG       1500

ATGGACCATA TGCTTGGGGG CTGTGCTTCA AGGAAGAAGT TAGTCCTCAA       1550

AGTGATTATT GTGATTCCTC CAACAAAGAA TGGCCCTGTT ATCCTGGAAA       1600

GAGTTACAAA GGCAGAGGAC CAATTCAACT TTCCTGGTAT ATAATATATA       1650

AATCTTTCAT ATTTGCATGT TTTTACATCC ATTATATTAT TTGCACTCCA       1700

AGAAAGTTAT GGTCCATTTA CATACTAACT CTTCTCCTGT GAGATTAGAT       1750

TGTGGATTTT TCTCATTTTG CATTCATCTA ATTTTTTTTT CATGTTTAAG       1800

TATGATAAGT ATATATGCAG TTGAATTATC AATTATATTA GTAATTAAGT       1850

TTCTTTTCAT CTTGTTTGCG ATACTGTGTT CAACTCACTA ATAAATGCCA       1900

ATTTAATAGA CAAACAACAT TTTTGTTTCT ATATTATTAT TTTGACTAAA       1950

GATGTTTACT TAATATGACC TTGTCTTCTT TAATTATAAT TAGTGAAAAT       2000

ATCAAATCTC TCAAATTATT TAATAATTTC TAACTATCAA TTTCACATAA       2050

AATTAATTGT ACTTGAGTTT CTACCTTTTT AAATAGTACT AAAAAAATAA       2100

AAATAATATT TACTAATCGT ACTGAATTCT TAAAAAAAGA AACACAATAT       2150

GATGTGCATT TTTAATTAAA TATTGAATTT AATTTTTATA TATTATTAGT       2200

ATAAAATTTT TTACACATAA TTAATTGTGT ATTGTTATAT CAATAGAAAT       2250

AATTAATTTT TACATTGTTA GTATATTAAA ATTAAAAAAT TATCTAAATA       2300

TATAAATATT ATCAAATAAT CTATTTACAT TATTAGTGTC TCAAAATTAA       2350

AATCCTCATA TATTTATTTT TTAATTCATG ACAAAAAAAA GACATGTGAA       2400

TAAAACTCTA CTATATTCTT AGGGGATTGG ATGTCCACAA CTAATATGCC       2450

ATTTGTGCCA AGTCTCAGCT GCCTGCTTGC GTGATTGTTT AGATTATTCA       2500

AATGTGAAAG CCAATTGTTG CATGGATGTA CTTACTCTTT CTTTTTTTGT       2550

GTTAGGAATT ACAACTATGG GCCAGCAGGG AAGGCCTTGG GATTCGATGG       2600
```

| | |
|---|---:|
| CCTTAAGAAC CCAGACATTG TGTCAAACAA TTCAGTAATT GCATTCAAAA | 2650 |
| CAGCACTCTG GTTTTGGATG ACAGAGCAGA AACCAAAACC TTCTTGCCAC | 2700 |
| AACGTCATGG TTGGGAATTA CGTGCCAACA GCATCTGATA GAGCAGCAAA | 2750 |
| TAGAACCTTA GGGTTTGGGT TGGTTACTAA CATAATCAAC GGTGGACTTG | 2800 |
| AATGTGGAGT TCCAGATGAT GCAAGAGTCA ATGATCGGAT TGGATACTTT | 2850 |
| CAAAGATATG CTAAGTTGTT TAATGTAGAT ACTGGACCTA ACTTGGATTG | 2900 |
| TGCATATCAG AAATCCTTCT AAGCTTACAT TGTTTTTGGT GTATCCTTTC | 2950 |
| TTTTTCTTTT GTTTCTATAA TTTTCTCTAT TTAGTAAATG GTCAAATTCA | 3000 |
| TTTTTAAAAG ATTATTTATG TTTAAATTGA TCTTCGAAAA ATTATTCAGC | 3050 |
| TTTTAAAAAT TTTAAATTGG TCACATTAAT CCCTCTGTCA CTTTCATTTT | 3100 |
| TCGTGGCATC AAAATTTGTT GATATGACAC TTTAAGTGAC ACTACAACAG | 3150 |
| ATATCTGACA ATTCTAATTA GGTGCTAATA TGATAAATTT ATGAAATTAG | 3200 |
| ACCAAATCAA TCCTAATTTG AAAATTTTCA ATGTCTCAAA ATCTTGTTGA | 3250 |
| AGTTAGGGTT GATTTCATCT AATTGCATAA ATTTAGTATG TTAACAATCA | 3300 |
| ATTAGGACAG CTAGGAATAT ACTATGGTCA ATATGGTGTC ACTTCGTCAA | 3350 |
| CAATGAAAAT GACAAAATGA CTAATATAAC TAATTTAAAA TATTTGAAAA | 3400 |
| ATAAATTTGA TT | 3412 |

(2) INFORMATION FOR SEQ ID NO: 4:

(i) SEQUENCE CHARACTERISTICS:
        (A) LENGTH: 1169 nucleotides
        (B) TYPE: Nucleic acid
        (C) STRANDEDNESS: Double
        (D) TOPOLOGY: Linear (ii) MOLECULE TYPE: Genomic DNA (vi) ORIGINAL SOURCE:
        (A) ORGANISM: Peanut (arachis hypogaea)

(xi) SEQUENCE DESCRIPTION: SEQ ID NO:4:

| | |
|---|---:|
| ATCGATACCA TGTGTCCATA TTTTTATACT TTTAGCCTCA AATTCTTTCA | 50 |
| TTTCTTAAGA GTATAAAGAC ATAATATTAT CTATCAACCT ATTATATTAT | 100 |
| TATTAGGGTG GCATGTATGC ATAGGTTCTA TGGCTAGTCT CGTATTTATT | 150 |
| CAAAGGTGAA TTTTAACAAA ACTATGAATG GTATAGTTTT TAAATGGGTT | 200 |
| TATAAGTGTT AGTCATTCCT CGCTTTTTGA ATTAGTTTTT TGAATTGAGG | 250 |
| TAGACTCGTT CAAACTCAAT TTTAATATAA GAAAAAAAAT ATTAAGGATG | 300 |
| TTACAAATAA AAATTTTAAT AAACAATATT ACTTTTTAAA AATTTTCAAT | 350 |
| ACAATAAAAT GTATGGAAAA ATGCTAAAAC TTTTTATTTT ACCTTCGTTA | 400 |
| ACTAATGCCG AAAGTCCAAT CCCATTTTCC TCCATTCATG GACTATGTCA | 450 |
| ATGTGACATG ATAATGATGG TTATCAAGAA CTCAAATTTT AGTACAACTG | 500 |
| GTATAAAAAA ATATTGAAAG TAATAGATAG ATTTGAGAAG TGAAATCAAA | 550 |
| TTATACATGA ATTGAAGAAT GACTCTGAAA CATCTTATTA ATCTCTTCCA | 600 |
| CCTCCACAAT GATATCACAC ACTCCAATTC ATAAATAAAA ACATAATTTT | 650 |
| TTATGCATCT TTTAATAATT TCAAAGTCTT ATGTTTAAGA TAGGAGGGCA | 700 |
| AAGATAACAA CAATATATGA TGGAAGCTTC AGAAAGTCAA AACTAGTTTA | 750 |

-continued

```
GTCATCATTT TATATAAACT TGGAATGGTC CTCTCAATTA AATATGAGAG          800

AAGGATTCAA AGCCGAAAAC ATTTCTTTAA TTTTCATTCA AGTTCTCTAT          850

TATGTTACAA ATTTAGTATC AACAAATTAA TAACAAAGAA ATACATTATG          900

AAGCAGCTTG CCAAGTAGGA ACACACTAAA TGGGTTTCAT AATAAATGAT          950

GAACATATAA TGCGTTAGTG AGTAGGACAA CATAAACCGT TGACCTTTGA         1000

CCCTCCACGC CCACTAAGCC ACCACCGTCT TTTACCTTTG AATATACGAA         1050

ATCTTTGTGT AGCGTTGAGT ATTGATTATT GAAATTGTAC ATATATAAAC         1100

CTTAATCCTA CCTCATATCA TTCCCACATA AAAACCAAAC CAATCCTTGA         1150

TAACATAACA TCCAATAAC                                           1169
```

What is claimed is:

1. An isolated and purified DNA fragment comprising a nucleotide sequence selected from the group consisting of:

(i) the nucleotide sequence:

```
ATCTCGTTCA AGTCGGCGCT CTGGTTGTGG ATGACAGAGC  40

AGAAACCAAA ACCTTCTTGC CACAACGTCA TGGTTGGGAA  80

TTACGTGCCA ACAGCATCTG ATAGAGCAGC AAATAGAACC 120

TTAGGGTTTG GGTTGGTTAC GAACATCATC AACGGCGGCC 160

TGGACTGCGG                                  170
``` which has been designated SEQ ID NO: 1; or (ii) a hybridizing nucleotide sequence that hybridizes to the nucleotide sequence in (i) under stringent conditions in a plaque hybridization assay of genomic *Arachis hypogaea* DNA using the nucleotide sequence in (i) as a probe, expression of said hybridizing nucleotide sequence being inducible by a pathogen, and said hybridizing nucleotide sequence, when introduced into and expressed in a plant, conferring on said plant an increased resistance to a pest as compared to an untransformed plant of the same plant species exposed to the same pest under the same conditions, said increased resistance to said pest being a result of the expression of said hybridizing nucleotide sequence.

2. An isolated and purified DNA fragment according to claim 1, encoding a gene, said gene comprising a regulatory region and a protein coding region, expression of said gene being inducible by a pathogen.

3. An isolated and purified DNA fragment according to claim 2, comprising a protein coding region which encodes a hydrolase.

4. An isolated and purified cDNA comprising a nucleotide sequence selected from the group consisting of:

(i) the nucleotide sequence:

```
ATCTCGTTCA AGTCGGCGCT CTGGTTGTGG ATGACAGAGC  40

AGAAACCAAA ACCTTCTTGC CACAACGTCA TGGTTGGGAA  80

TTACGTGCCA ACAGCATCTG ATAGAGCAGC AAATAGAACC 120
```

-continued

```
TTAGGGTTTG GGTTGGTTAC GAACATCATC AACGGCGGCC 160

TGGACTGCGG                                  170
``` which has been designated SEQ ID NO: 1; or (ii) a hybridizing nucleotide sequence that hybridizes to the nucleotide sequence in (i) under stringent conditions in a plaque hybridization assay of genomic *Arachis hypogaea* DNA using the nucleotide sequence in (i) as a probe, expression of said hybridizing nucleotide sequence being inducible by a pathogen, and said hybridizing nucleotide sequence, when introduced into and expressed in a plant, conferring on said plant an increased resistance to a pest as compared to an untransformed plant of the same plant species exposed to the same pest under the same conditions, said increased resistance to said pest being a result of the expression of said hybridizing nucleotide sequence.

5. An isolated and purified DNA fragment comprising one strand consisting of a nucleotide sequence selected from the group consisting of:

(i) the nucleotide sequence:

```
ATCGATACCA TGTGTCCATA TTTTTATACT TTTAGCCTCA  40

AATTCTTTCA TTTCTTAAGA GTATAAAGAC ATAATATTAT  80

CTATCAACCT ATTATATTAT TATTAGGGTG GCATGTATGC 120

ATAGGTTCTA TGGCTAGTCT CGTATTTATT CAAAGGTGAA 160

TTTTAACAAA ACTATGAATG GTATAGTTTT TAAATGGGTT 200

TATAAGTGTT AGTCATTCCT CGCTTTTTGA ATTAGTTTTT 240

TGAATTGAGG TAGACTCGTT CAAACTCAAT TTTAATATAA 280

GAAAAAAAAT ATTAAGGATG TTACAAATAA AAATTTTAAT 320

AAACAATATT ACTTTTTAAA AATTTTCAAT ACAATAAAAT 360

GTATGGAAAA ATGCTAAAAC TTTTTATTTT ACCTTCGTTA 400

ACTAATGCCG AAAGTCCAAT CCCATTTTCC TCCATTCATG 440

GACTATGTCA ATGTGACATG ATAATGATGG TTATCAAGAA 480

CTCAAATTTT AGTACAACTG GTATAAAAAA ATATTGAAAG 520
```

-continued

```
TAATAGATAG ATTTGAGAAG TGAAATCAAA TTATACATGA    560

ATTGAAGAAT GACTCTGAAA CATCTTATTA ATCTCTTCCA    600

CCTCCACAAT GATATCACAC ACTCCAATTC ATAAATAAAA    640

ACATAATTTT TTATGCATCT TTTAATAATT TCAAAGTCTT    680

ATGTTTAAGA TAGGAGGGCA AAGATAACAA CAATATATGA    720

TGGAAGCTTC AGAAAGTCAA AACTAGTTTA GTCATCATTT    760

TATATAAACT TGGAATGGTC CTCTCAATTA AATATGAGAG    800

AAGGATTCAA AGCCGAAAAC ATTTCTTTAA TTTTCATTCA    840

AGTTCTCTAT TATGTTACAA ATTTAGTATC AACAAATTAA    880

TAACAAAGAA ATACATTATG AAGCAGCTTG CCAAGTAGGA    920

ACACACTAAA TCGTTTCAT AATAAATGAT GAACATATAA     960

TGCGTTAGTG AGTAGGACAA CATAAACCGT TGACCTTTGA   1000

CCCTCCACGC CCACTAAGCC ACCACCGTCT TTTACCTTTG   1040

AATATACGAA ATCTTTGTGT AGCGTTGAGT ATTGATTATT   1080

GAAATTGTAC ATATATAAAC CTTAATCCTA CCTCATATCA   1120

TTCCCACATA AAAACCAAAC CAATCCTTGA TAACATAACA   1160

TCCAATAAC                                     1169
``` which has been designated SEQ ID NO: 4; or (ii) a hybridizing nucleotide sequence that hybridizes to the nucleotide sequence in (i) under stringent conditions in a plaque hybridization assay of genomic *Arachis hypogaea* DNA using the nucleotide sequence in (i) as a probe, said hybridizing nucleotide sequence, when operably linked to a cDNA according to claim 4 and introduced into a plant, being inducible by a pathogen, and resulting in the expression of said cDNA in said plant, thereby conferring on said plant an increased resistance to a pest as compared to an untransformed plant of the same plant species exposed to the same pest under the same conditions, said increased resistance to said pest being a result of the expression of said cDNA.

6. Isolated DNA having the nucleotide sequence:

```
ATCTCGTTCA AGTCGGCGCT CTGGTTGTGG ATGACAGAGC     40

AGAAACCAAA ACCTTCTTGC CACAACGTCA TGGTTGGGAA     80

TTACGTGCCA ACAGCATCTG ATAGAGCAGC AAATAGAACC    120

TTAGGGTTTG GGTTGGTTAC GAACATCATC AACGGCGGCC    160

TGGACTGCGG                                     170
``` which has been designated SEQ ID NO: 1.

7. Procaryotic or eucaryotic DNA comprising a DNA fragment according to claim 1.

8. A vector comprising the DNA fragment according to claim 1.

9. A vector according to claim 8, which is plasmid pR 3-7.

10. Microorganisms comprising the DNA fragment according to claim 1.

11. Microorganisms according to claim 10, which are *Escherichia coli* strain RG-2 (DSM 6149).

12. Transformed plant cells according to claim 11, which are protoplasts.

13. An isolated and purified DNA fragment according to claim 12, which consists of the nucleotide sequence:

```
ATCGATACCA TGTGTCCATA TTTTTATACT TTTAGCCTCA AATTCTTTCA    50

TTTCTTAAGA GTATAAAGAC ATAATATTAT CTATCAACCT ATTATATTAT   100

TATTAGGGTG GCATGTATGC ATAGGTTCTA TGGCTAGTCT CGTATTTATT   150

CAAAGGTGAA TTTTAACAAA ACTATGAATG GTATAGTTTT TAAATGGGTT   200

TATAAGTGTT AGTCATTCCT CGCTTTTTGA ATTAGTTTTT TGAATTGAGG   250

TAGACTCGTT CAAACTCAAT TTTAATATAA GAAAAAAAAT ATTAAGGATG   300

TTACAAATAA AAATTTTAAT AAACAATATT ACTTTTTAAA AATTTTCAAT   350

ACAATAAAAT GTATGGAAAA ATGCTAAAAC TTTTTATTTT ACCTTCGTTA   400

ACTAATGCCG AAAGTCCAAT CCCATTTTCC TCCATTCATG GACTATGTCA   450

ATGTGACATG ATAATGATGG TTATCAAGAA CTCAAATTTT AGTACAACTG   500

GTATAAAAAA ATATTGAAAG TAATAGATAG ATTTGAGAAG TGAAATCAAA   550

TTATACATGA ATTGAAGAAT GACTCTGAAA CATCTTATTA ATCTCTTCCA   600

CCTCCACAAT GATATCACAC ACTCCAATTC ATAAATAAAA ACATAATTTT   650

TTATGCATCT TTTAATAATT TCAAAGTCTT ATGTTTAAGA TAGGAGGGCA   700

AAGATAACAA CAATATATGA TGGAAGCTTC AGAAAGTCAA AACTAGTTTA   750

GTCATCATTT TATATAAACT TGGAATGGTC CTCTCAATTA AATATGAGAG   800

AAGGATTCAA AGCCGAAAAC ATTTCTTTAA TTTTCATTCA AGTTCTCTAT   850

TATGTTACAA ATTTAGTATC AACAAATTAA TAACAAAGAA ATACATTATG   900
```

-continued

```
AAGCAGCTTG CCAAGTAGGA ACACACTAAA TGGGTTTCAT AATAAATGAT  950

GAACATATAA TGCGTTAGTG AGTAGGACAA CATAAACCGT TGACCTTTGA 1000

CCCTCCACGC CCACTAAGCC ACCACCGTCT TTTACCTTTG AATATACGAA 1050

ATCTTTGTGT AGCGTTGAGT ATTGATTATT GAAATTGTAC ATATATAAAC 1100

CTTAATCCTA CCTCATATCA TTCCCACATA AAAACCAAAC CAATCCTTGA 1150

TAACATAACA TCCAATAACA TGGCATTATT CTCATTCTCA TTCTCCTCAT 1200

TCTGCCTCAC AATTTTTGTC ATCTATTCTT CTTTATCTCT ATCTGCTGAA 1250

TCACGTGTCT CACCAATTGC ACCAATCTCT TCTCTCATTA GCAAAACCCT 1300

TTTCGACTCA ATCTTTTTAC ATAAAGATGA CAATGCTTGC CCTGCTAGAA 1350

ACTTTTACAC TTATGAATCC TTCGTTGAGG CAACCTCGAG CTTCCCAGCG 1400

TTCGGCTCGA CCGGATGCTC GGCCACACGG AAGCGCGAGG TTGCCGCATT 1450

TCTTGCACAG ATCTCACATG AAACCACAGG TGGTTGGGCT ACTGCACCTG 1500

ATGGACCATA TGCTTGGGGG CTGTGCTTCA AGGAAGAAGT TAGTCCTCAA 1550

AGTGATTATT GTGATTCCTC CAACAAAGAA TGGCCCTGTT ATCCTGGAAA 1600

GAGTTACAAA GGCAGAGGAC CAATTCAACT TTCCTGGTAT ATAATATATA 1650

AATCTTTCAT ATTTGCATGT TTTTACATCC ATTATATTAT TTGCACTCCA 1700

AGAAAGTTAT GGTCCATTTA CATACTAACT CTTCTCCTGT GAGATTAGAT 1750

TGTGGATTTT TCTCATTTTG CATTCATCTA ATTTTTTTTT CATGTTTAAG 1800

TATGATAAGT ATATATGCAG TTGAATTATC AATTTATATTA GTAATTAAGT 1850

TTCTTTTCAT CTTGTTTGCG ATACTGTGTT CAACTCACTA ATAAATGCCA 1900

ATTTAATAGA CAAACAACAT TTTTGTTTCT ATATTATTAT TTTGACTAAA 1950

GATGTTTACT TAATATGACC TTGTCTTCTT TAATTATAAT TAGTGAAAAT 2000

ATCAAATCTC TCAAATTATT TAATAATTTC TAACTATCAA TTTCACATAA 2050

AATTAATTGT ACTTGAGTTT CTACCTTTTT AAATAGTACT AAAAAAATAA 2100

AAATAATATT TACTAATCGT ACTGAATTCT TAAAAAAAGA AACACAATAT 2150

GATGTGCATT TTTAATTAAA TATTGAATTT AATTTTTATA TATTATTAGT 2200

ATAAAATTTT TTACACATAA TTAATTGTGT ATTGTTATAT CAATAGAAAT 2250

AATTAATTTT TACATTGTTA GTATATTAAA ATTAAAAAAT TATCTAAATA 2300

TATAAATATT ATCAAATAAT CTATTTACAT TATTAGTGTC TCAAAATTAA 2350

AATCCTCATA TATTTATTTT TTAATTCATG ACAAAAAAAA GACATGTGAA 2400

TAAAACTCTA CTATATTCTT AGGGGATTGG ATGTCCACAA CTAATATGCC 2450

ATTTGTGCCA AGTCTCAGCT GCCTGCTTGC GTGATTGTTT AGATTATTCA 2500

AATGTGAAAG CCAATTGTTG CATGGATGTA CTTACTCTTT CTTTTTTTGT 2550

GTTAGGAATT ACAACTATGG GCCAGCAGGG AAGGCCTTGG GATTCGATGG 2600

CCTTAAGAAC CCAGACATTG TGTCAAACAA TTCAGTAATT GCATTCAAAA 2650

CAGCACTCTG GTTTTGGATG ACAGAGCAGA AACCAAAACC TTCTTGCCAC 2700

AACGTCATGG TTGGGAATTA CGTGCCAACA GCATCTGATA GAGCAGCAAA 2750

TAGAACCTTA GGGTTTGGGT TGGTTACTAA CATAATCAAC GGTGGACTTG 2800

AATGTGGAGT TCCAGATGAT GCAAGAGTCA ATGATCGGAT TGGATACTTT 2850

CAAAGATATG CTAAGTTGTT TAATGTAGAT ACTGGACCTA ACTTGGATTG 2900
```

```
                                                       -continued
TGCATATCAG AAATCCTTCT AAGCTTACAT TGTTTTTGGT GTATCCTTTC 2950

TTTTTCTTTT GTTTCTATAA TTTTCTCTAT TTAGTAAATG GTCAAATTCA 3000

TTTTTAAAAG ATTATTTATG TTTAAATTGA TCTTCGAAAG ATTATTCAGC 3050

TTTTAAAAAT TTTAAATTGG TCACATTAAT CCCTCTGTCA CTTTCATTTT 3100

TCGTGGCATC AAAATTTGTT GATATGACAC TTTAAGTGAC ACTACAACAG 3150

ATATCTGACA ATTCTAATTA GGTGCTAATA TGATAAATTT ATGAAATTAG 3200

ACCAAATCAA TCCTAATTTG AAAATTTTCA ATGTCTCAAA ATCTTGTTGA 3250

AGTTAGGGTT GATTTCATCT AATTGCATAA ATTTAGTATG TTAACAATCA 3300

ATTAGGACAG CTAGGAATAT ACTATGGTCA ATATGGTGTC ACTTCGTCAA 3350

CAATGAAAAT GACAAAATGA CTAATATAAC TAATTTAAAA TATTTGAAAA 3400

ATAAATTTGA TT                                         3412
``` which has been designated SEQ ID NO:3.

14. The isolated and purfied DNA fragment according to claim 1, which consists of a protein coding sequence.

15. A transformed plant cell comprising within its genome a DNA fragment according to claim 1, wherein said DNA fragment is expressed when said transformed plant cell is exposed to a pest, said transformed plant cell exhibiting increased resistance to said pest as compared to an untransformed plant cell of the same cell type and plant species exposed to the same pest under the same conditions, and said increased resistance to said pest being a result of the expression of said DNA fragment.

16. A transformed whole plant comprising within its genome a DNA fragment according to claim 1, wherein said DNA fragment is expressed when said transformed whole plant is exposed to a pest, said transformed whole plant exhibiting increased resistance to said pest as compared to an untransformed whole plant of the same plant species exposed to the same pest under the same conditions, and said increased resistance to said pest being a result of the expression of said DNA fragment.

17. A transformed plant part comprising within its genome a DNA fragment according to claim 1, wherein said DNA fragment is expressed when said transformed plant part is exposed to a pest, said transformed plant part exhibiting increased resistance to said pest as compared to an untransformed plant part of the same part type and plant species exposed to the same pest under the same conditions, and said increased resistance to said pest being a result of the expression of said DNA fragment.

18. A transformed plant seed comprising within its genome a DNA fragment according to claim 1, wherein said DNA fragment is expressed when said transformed plant seed is exposed to a pest, said transformed plant seed exhibiting increased resistance to said pest as compared to an untransformed plant seed of the same plant species exposed to the same pest under the same conditions, and said increased resistance to said pest being a result of the expression of said DNA fragment.

19. An isolated and purified DNA fragment comprising a resistance gene and isolatable from *Arachis hypogaea* by a process comprising the following steps:
   (i) isolating total genomic DNA from *Arachis hypogaea*;
   (ii) cleaving said total genomic DNA into fragments with a restriction endonuclease;
   (iii) cloning said fragments into vectors; and
   (iv) identifying said DNA fragment containing a resistance gene by hydridizing said vectors under stringent conditions with a probe comprising a DNA sequence comprising the nucleotide sequence:

```
ATCTCGTTCA AGTCGGCGCT CTGGTTGTGG ATGACAGAGC  40

AGAAACCAAA ACCTTCTTGC CACAACGTCA TGGTTGGGAA  80

TTACGTGCCA ACAGCATCTG ATAGAGCAGC AAATAGAACC 120

TTAGGGTTTG GGTTGGTTAC GAACATCATC AACGGCGGCC 160

TGGACTGCGG                                  170
``` which has been designated SEQ ID NO: 1.

20. A process comprising the following steps:
   (a) isolating total genomic DNA from *Arachis hypogaea*;
   (b) cleaving said total genomic DNA into fragments with a restriction endonuclease;
   (c) cloning said fragments into vectors; and
   (d) identifying said DNA fragment containing a resistance gene by hydridizing said vectors under stringent conditions with a probe comprising a DNA sequence according to claim 6,
   (e) optionally isolating said resistence gene identified in (d);
   (f) optionally isolating a protein coding sequence of the resistence gene identified in (d); and
   (g) optionally isolating a regulatory sequence of the resistence gene identified in (d).

* * * * *